(12) United States Patent
Canady et al.

(10) Patent No.: US 12,048,704 B2
(45) Date of Patent: *Jul. 30, 2024

(54) METHOD FOR TREATMENT OF CANCER WITH COMBINATION OF COLD ATMOSPHERIC PLASMA AND A GENE INHIBITOR

(71) Applicant: Jerome Canady Research Institute for Advanced Biological and Technological Sciences, Takoma Park, MD (US)

(72) Inventors: Jerome Canady, Lakeland, FL (US); Saravana Murthy, Fairfax, VA (US); Xiaoqian Cheng, Owings Mills, MD (US); Taisen Zhuang, Rockvillle, MD (US)

(73) Assignee: Jerome Canady Research Institute for Advanced Bio, Takoma Park, MD (US)

( * ) Notice: Subject to any disclaimer, the term of this patent is extended or adjusted under 35 U.S.C. 154(b) by 771 days.

This patent is subject to a terminal disclaimer.

(21) Appl. No.: 17/135,883

(22) Filed: Dec. 28, 2020

(65) Prior Publication Data

US 2021/0196727 A1    Jul. 1, 2021

Related U.S. Application Data

(60) Provisional application No. 62/953,754, filed on Dec. 26, 2019.

(51) Int. Cl.
*A61K 31/551* (2006.01)
*A61K 35/16* (2015.01)

(52) U.S. Cl.
CPC ............ *A61K 31/551* (2013.01); *A61K 35/16* (2013.01)

(58) Field of Classification Search
CPC ........ A61B 18/042; A61B 2018/00583; A61K 31/551; A61P 35/00
See application file for complete search history.

(56) References Cited

U.S. PATENT DOCUMENTS

| | | |
|---|---|---|
| 9,999,462 B2 | 6/2018 | Canady et al. |
| 10,023,858 B2 | 7/2018 | Canady et al. |
| 10,213,614 B2 | 2/2019 | Keidar et al. |
| 10,329,535 B2 | 6/2019 | Trink et al. |
| 10,405,913 B2 | 9/2019 | Canady et al. |
| 2014/0378892 A1 | 12/2014 | Keidar et al. |
| 2017/0183631 A1 | 6/2017 | Keidar et al. |
| 2018/0271579 A1 | 9/2018 | Keidar et al. |

FOREIGN PATENT DOCUMENTS

WO    2018191265 A1    10/2018

OTHER PUBLICATIONS

Montserrat Perez-Salvia et al. Epigenetics, 2017, 323-339.*
F. Bray, J. Ferlay, I. Soerjomataram, R.L. Siegel, L.A. Torre, A. Jemal, "Global cancer statistics 2018: GLOBOCAN estimates of incidence and mortality worldwide for 36 cancers in 185 countries," CA Cancer J Clin, 68 (2018) 394-424).
N. Howlader, K.A. Cronin, A.W. Kurian, R. Andridge, "Differences in Breast Cancer Survival by Molecular Subtypes in the United States," Cancer Epidemiol Biomarkers Prev, 27 (2018) 619-626).

* cited by examiner

*Primary Examiner* — Shobha Kantamneni
(74) *Attorney, Agent, or Firm* — 24IP Law Group USA, PLLC; Timothy R DeWitt

(57) ABSTRACT

A method for treating cancer. The method comprises treating a patient having a cancerous tumor with a gene inhibitor pre-operatively to inhibit upregulation of a particular gene, surgically removing the cancerous tumor, treating the patient with the gene inhibitor intra-operatively to inhibit upregulation of a particular gene, applying cold atmospheric plasma to surgical margins around the area in the patient from which the tumor was surgically removed, and treating the patient with the gene inhibitor post-operatively.

6 Claims, 20 Drawing Sheets

Specification includes a Sequence Listing.

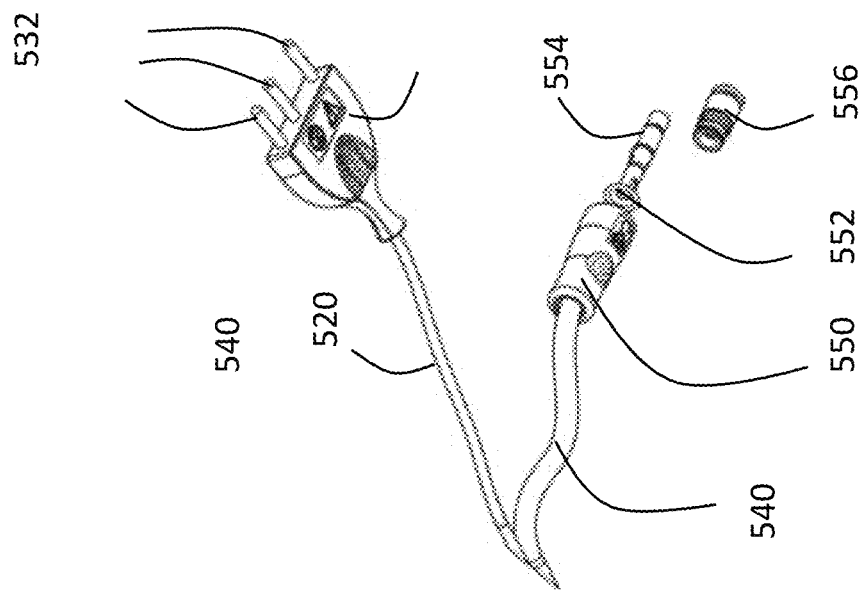

Table 1

| Category | Gene Class | Gene name | Gene Symbol | Forward primer | Reverse primer |
|---|---|---|---|---|---|
| Induction of Apoptosis | Death Domain Receptors | CASP2 and RIPK1 domain containing adaptor with death domain | CRADD | CATCAGACCGGCAGATTAACC | GTTGGCCTTACAGCGGGTAGAT |
| | | Fas associated via death domain | FADD | GTGGCTGACCTGGTACAAGAG | GGTAGATGCGTCTGAGTTCCAT |
| | | Tumor Necrosis Factor | TNF | GAGGCCAAGCCCTGGTATG | CGGGCCGATTGATCTCAGC |
| | | TNF receptor superfamily member 10b | TNFRSF10B | ACAGTTGCAGCCGTAGTCTTG | CCAGGTCGTTGTGAGCTTCT |
| | DNA Damage & Repair | ABL proto-oncogene 1, non-receptor tyrosine kinase | ABL1 | TGAAAAGCTTCCGGGTCTTAGG | TTGACTGGCGTGATGTAGTTG |
| | | Cell death inducing DFFA like effector a | CIDEA | CTTGGGAGACAACACGCATTT | TCTCGCTATTCCCGACCTCTT |
| | | Cell death inducing DFFA like effector b | CIDEB | CAGCGACCTTTCCGTGTCT | GGGTCTCCAATGCTTTGGCT |
| | | Tumor Protein p53 | TP53 | GAGGTTGGCTCTGACTGTACC | TCCGTCCCAGTAGATTACCAC |
| | | Tumor Protein p73 | TP73 | CGGGCCATGCCTGTTTACA | TGTCCTTCGTTGAAGTCCCTC |
| | Extracellular Apoptotic Signals | CASP8 and FADD like apoptosis regulator | CFLAR | | |
| | | Death associated protein kinase 1 | DAPK1 | GAGTTTGTCGCTCCTGAGATAGT | GCTTAGTGTCTCCAAGAAATGGG |
| | | TNF receptor superfamily member 25 | TNFRSF25 | TCCCGCAGAGATACTGACTGT | GGACCCAGAACACACCTACTC |

FIG. 7

Table 2

| Category | Gene Class | Gene name | Gene Symbol | Forward primer | Reverse primer |
|---|---|---|---|---|---|
| Regulation of Apoptosis | Positive Regulation of Apoptosis | ABL proto-oncogene 1, non-receptor tyrosine kinase | ABL1 | TGAAAAGCTCCGGGTCTTAGG | TTGACTGGCGTGATGTAGTTG |
| | | AKT serine/threonine kinase 1 | AKT1 | GTCATCGAACGCACCTTCCAT | AGCTTCAGGTACTCAAACTCGT |
| | | BCL2 associated agonist of cell death | BAD | CCCAGAGTTTGAGCCGAGTG | CCCATCCCTTCGTCGTCCT |
| | | BCL2 antagonist/killer 1 | BAK1 | ATGGTCACCTTACCTCTGCAA | TCATAGGGTCGGTTGATGTCG |
| | | BCL2 associated X, apoptosis regulator | BAX | CCCGAGAGGTCTTTTTCCGAG | CCAGCCCATGATGGTTCTGAT |
| | | BCL2 like 11 | BCL2L11 | TAAGTTCTGAGTGTGACCGAGA | GCTCTGTCTGTAGGGAGGTAGG |
| | | BH3 interacting domain death agonist | BID | ATGGACCGTAGCATCCCTCC | GTAGGTGCGTAGGTTCTGGT |
| | | BCL2 interacting killer | BIK | GACCTGGACCCTATGGAGGAC | CCTCAGTCTGTCGTAGATGA |
| | | BCL2 interacting protein 3 | BNIP3 | CAGGGCTCCTGGGTAGAACT | CTACTCCGTCCAGACTCATGC |
| | | BCL2 interacting protein 3 like | BNIP3L | TTGGATGCACAACATGAATCAGG | TCTTCTGACTGAGGAGCTATGGTC |
| | Negative Regulation of Apoptosis | BCL2 associated athanogene 1 | BAG1 | AGAGGTCATAGGGGTTCCACA | GCTGACAACGGTGTTTCCATT |
| | | BCL2 associated athanogene 3 | BAG3 | ATTCCGGTGATACGAGCAG | GCTGGTGGGTCTGGTACTC |
| | | BCL10, immune signaling adaptor | BCL10 | TCTGACACCCTTGTTGAATCT | TGGAAAAGGTTCACAACTGCTAC |
| | | BCL2, apoptosis regulator | BCL2 | GGTGGGGTCATGTGTGTGG | CGGTTCAGGTACTCAGTCATCC |
| | | BCL2 related protein A1 | BCL2A1 | TACAGGCTGGCTCAGGACTAT | CGCAACATTTTGTAGCACTCTG |
| | | BCL2 like 1 | BCL2L1 | GAGCTGGTGGTTGACTTTCTC | TCCATCTCCGATTCAGTCCCT |
| | | BCL2 like 10 | BCL2L10 | | |
| | | BCL2 like 2 | BCL2L2 | GCGGAGTTCACAGCTCTATAC | AAAAGGCCCTACAGTTACCA |
| | | Bifunctional apoptosis regulator | BFAR | TTCCTTTAGCTCCTAACACAGGC | TGCTGCTCCAGTGATAGAGCA |
| | | Baculoviral IAP repeat containing 2 | BIRC2 | GTTCAGTGGTTCTTCTTACTCCAGC | ACTGTAGGGGTTAGTCTCGAT |
| | | Baculoviral IAP repeat containing 3 | BIRC3 | TTTCCGTGGCTCTTATTCAAACT | GCACAGTGGTAGGAACTTCTCAT |
| | | Baculoviral IAP repeat containing 6 | BIRC6 | TAGTGTATGCCTCGTTTGTTGG | TTCTGTGTGCTCACCTTTC |
| | | BCL2 interacting protein 2 | BNIP2 | TGGCTCCCTGGATTATCAAGA | CCAGTGTCAGGCTAATGTCTG |
| | | BCL2 interacting protein 3 | BNIP3 | | |
| | | BCL2 interacting protein 3 like | BNIP3L | | |
| | | B-Raf proto-oncogene, serine/threonine kinase | BRAF | TGGGAACGGAACTGATTTTC | TTTTGTGGTGACTTGGGGTTG |
| | | Caspase 3 | CASP3 | | |
| | | CD27 molecule | CD27 | | |
| | | CD40 ligand | CD40LG | GAGCAACAACTTGGTAACCCT | GGCTGGCTATAAATGGAGCTTG |
| | | CASP8 and FADD like apoptosis regulator | CFLAR | | |
| | | Cell death inducing DFFA like effector a | CIDEA | CTTGGGAGAGACAACACGCATTT | TCTCGCTATTCCCGACCTCTT |
| | | Death associated protein kinase 1 | DAPK1 | | |
| | | DNA fragmentation factor subunit alpha | DFFA | GGACCTCCAGATGCTTGTTGA | GGAGCTGCTTGGACTGACG |
| | | Fas cell surface death receptor | FAS | TCTGGTTCTTACGTCGTTGC | CTGTAGGTCCCTAGCTTTCC |
| | | Insulin like growth factor 1 receptor | IGF1R | AGGATATTGGGCTTTACAACCTG | GAGGTAACAGAGGTCAGCATTTT |
| | | MCL1, BCL2 family apoptosis regulator | MCL1 | GTGCCTTTGTGGCTAAAACAT | AGTCCCGTTTTGTCCTTACGA |
| | | NLR family apoptosis inhibitory protein | NAIP | AAGGGGATTTGTTGACATAACGGG | CAGCCGTAGTTCTTCGTAAGC |
| | | Nucleolar protein 3 | NOL3 | GACCCAGCTATGACCCTC | CTCCGGTTCAGCCTCTTTAGA |
| | | Tumor Protein p53 | TP53 | | |
| | | Tumor Protein p73 | TP73 | | |
| | | X-linked inhibitor of apoptosis | XIAP | | |

FIG. 8

Table 3

| Category | Gene Class | Gene name | Gene Symbol | Forward primer | Reverse primer |
|---|---|---|---|---|---|
| Caspases & Regulators | Caspases | Caspase 1 | CASP1 | TTTCCGCAAGGTTCGATTTTCA | GGCATCTGCGCTCTACCATC |
| | | Caspase 10 | CASP10 | AGAAACCTGCTCTACGAACTGT | GGGAAGCGAGTCTTTCAGAAG |
| | | Caspase 14 | CASP14 | ACCATGAAAAGAGACCCCACT | GAGTACCACGAAGGCACAACT |
| | | Caspase 2 | CASP2 | AGCTGTTGTTGAGCGAATTGT | AGCAAGTTGAGGAGTTCCACA |
| | | Caspase 3 | CASP3 | GAAATTGTGGAATTGATGCGTGA | CTACAACGATCCCCTCTGAAAAA |
| | | Caspase 4 | CASP4 | CAAGAGAAGCAACGTATGGCA | AGGCAGATGGTCAAACTCTGTA |
| | | Caspase 5 | CASP5 | TTCAACACCACATAACGTGTCC | GTCAAGGTTGCTCGTTCTATGG |
| | | Caspase 6 | CASP6 | CACCAACATAACTGAGGTGGATG | AGGAGGAGCCATATTTTCCCA |
| | | Caspase 7 | CASP7 | AGTGACAGGTATGGGCGTTC | CGGCATTTGTATGGTCCTCTT |
| | | Caspase 8 | CASP8 | TCATGGACCACAGAGATTCGCAAAC | AGTGAACTGAGATGTCAGCTCAT |
| | | Caspase 9 | CASP9 | CTCAGACCAGAGATTCGCAAAC | GCATTTCCCCTCAAACTCTCAA |
| | | CASP8 and FADD like apoptosis regulator | CFLAR | AGGAGCAGGGACAAGTTACAG | GGACAATGGGCATAGGGTGTT |
| | | PYD and CARD domain containing | PYCARD | TGGATGCTCTGTACGGGAAG | CCAGGCTGGTGTGAAACTGAA |
| | Caspase Activation | Apoptosis inducing factor mitochondria associated 1 | AIFM1 | TTCCAGCGATGGCATGTTCC | TCCTACTGTTGATAAGCCCACA |
| | | Apoptotic peptidase activating factor 1 | APAF1 | AAGGTGGAGTACCACAGAGG | TCCATGTATGGTGACCCATCC |
| | | BCL2 associated X, apoptosis regulator | BAX | GCCAGGTTACGGCAGATTCA | GAAGGTCACGAGCGTCACC |
| | | BCL2 like 10 | BCL2L10 | | |
| | | Caspase 1 | CASP1 | | |
| | | Caspase 9 | CASP9 | | |
| | | Nucleotide binding oligomerization domain containing 1 | NOD1 | ACTGAAAAGCAATCGGGAACTT | CACCACAATCTCCGCATCTT |
| | | PYD and CARD domain containing | PYCARD | | |
| | | TNF receptor superfamily member 10b | TNFRSF10B | | |
| | | Tumor Protein p53 | TP53 | | |
| | Caspase Inhibition | CD27 molecule | CD27 | CAGAGAGGCACTACTGGGCT | CGGTATGCAAGGATCACACTG |
| | | X-linked inhibitor of apoptosis | XIAP | AATAGTGCCACGCAGTCTACA | CAGATGGCCTGTCTAAGGCAA |

FIG. 9

Table 4

| Category | Gene Class | Gene name | Gene Symbol | Forward primer | Reverse primer |
|---|---|---|---|---|---|
| Reactive Oxygen Species (ROS) Metabolism | Superoxide Dismutases (SOD) | superoxide dismutase 1 | SOD1 | GGTGGGCCAAAGGATGAAGAG | CCACAAGCCAAACGACTTCC |
| | | superoxide dismutase 2 | SOD2 | GGAAGCCATCAAACGTGACTT | CCCGTTCCTTATTGAAACCAAGC |
| | | superoxide dismutase 3 | SOD3 | ATGCTGGCGCTACTGTGTTC | CTCCGCCGAGTCAGAGTTG |
| | Other Superoxide Metabolism Genes: | Arachidonate 12-lipoxygenase, 12S type | ALOX12 | ATGCCCTCAAACGTGTTTAC | GCACTGGCGAACCTTCTCA |
| | | Copper chaperone for superoxide dismutase | CCS | ATCGAGGGAACTATTGACGGC | AGTTGTTTGTAAGGTCCCCGTA |
| | | Dual oxidase 1 | DUOX1 | GAGACCCCATGTTCGACCC | GGAATGCGAGGAACCATAGATG |
| | | Dual oxidase 2 | DUOX2 | ACGGTGTGTATCAGGCTCTG | CACGTCGGAAAGAAACATGGTAG |
| | | Metallothionein 3 | MT3 | acctcctgcaggaagaggctg | ctatctccacgtgctccaca |
| | | Neutrophil cytosolic factor 1 | NCF1 | GGGGCGATCAATCCAGAGAAC | GTACTCGGTAAGTGTGCCCTG |
| | | Neutrophil cytosolic factor 2 | NCF2 | CCAGAAGCATTAACCGAGACAA | CCTCGAAGCTGAATCAAGGC |
| | | Nitric oxide synthase 2 | NOS2 | TTCAGTATCACAACCTCAGCAAG | TGGACCTGCAAGTTAAAATCCC |
| | | NADPH oxidase 4 | NOX4 | CAGATGTTGGGGCTAGGATTG | GAGTGTTCGGCACATGGGTA |
| | | NADPH oxidase 5 | NOX5 | ACTCAGCAGTTTAAGACCATTGC | GGACTCTTTCACATGCAGAGC |
| | | Uncoupling protein 2 | UCP2 | GGAGGTGGTCGGAGATACCAA | ACAATGGCATTACGAGCAACAT |
| | Other Reactive Oxygen Species (ROS) Metabolism Genes: | Aldehyde oxidase 1 | AOX1 | ATGCCTGTCTGATTCCCATCT | CATGACACTTGGCAATCCTCT |
| | | BCL2 interacting protein 3 | BNIP3 | TGAGTCTGGACGGAGTAGCTC | CCCTGTTGGTATCTTGTGGTGT |
| | | Epoxide hydrolase 2 | EPHX2 | GACATCGGGGCTAATCTGAAG | GGCTTTACTGTCACGTACCCA |
| | | Mitochondrial inner membrane protein MPV17 | MPV17 | CTTTGCCCCGTGTTTTCTAGG | GGATAATCCCGCTGTAGTTTGG |
| | | Surfactant protein D | SFTPD | CCTTACAGGGACAAGTACAGCA | CTGTGCCTCCGTAAATGGTTT |
| | | Apolipoprotein E | APOE | GTTGCTGGTCACATTCCTGG | GCAGGTAATCCCAAAAGCGAC |
| | | Antioxidant 1 copper chaperone | ATOX1 | GTGCTGAAGCTGTCTCTCGG | GCCCAAGGTAGGAAACAGTCTTT |
| | | Catalase | CAT | TGGAGCTGGTAACCCACAGTAGG | CCTTTGCCTTGGAGTATTTGGTA |
| | | C-C motif chemokine ligand 5 | CCL5 | CCAGCAGTCGTCTTTGTCAC | CTCTGGGTTGGCACACACTT |
| | | Cytoglobin | CYGB | CCCGGCTCTATGCCAACTG | CCATGTGCTTGAACTGGCTGA |
| | | 24-dehydrocholesterol reductase | DHCR24 | CACTGTCTCACTACGTGTCGG | CCAGCCAATGGAGGTCAGC |
| | | Dual oxidase 1 | DUOX1 | | |
| | | Dual oxidase 2 | DUOX2 | | |
| | | Dual specificity phosphatase 1 | DUSP1 | GCCTTGCTTACCTTATGAGGAC | GGGAGAGATGATGCTTCGCC |
| | | Eosinophil peroxidase | EPX | CCAACCAGATTGTGCGCTTC | CGCAGGTCCTCTCACAGTC |
| | | Forkhead box M1 | FOXM1 | ATACGTGGATTGAGGACCACT | TCCAATGTCAAGTAGCGGTTG |
| | | Ferritin heavy chain 1 | FTH1 | TCCTACGTTTACCTGTCCATGT | GTTTGTGCAGTTCCAGTAGTGA |
| | | Glutamate-cysteine ligase catalytic subunit | GCLC | GGCACAAGGACGTTCTCAAGT | CAGACAGGACCAACCGGAC |
| | | Glutamate-cysteine ligase modifier subunit | GCLM | TGTCTTGGAATGCACTGTATCTC | CCCAGTAAGGCTGTAAATGCTC |
| | | Glutathione peroxidase 1 | GPX1 | CAGTCGGTGTATGCCTTCTCG | GAGGGACGCCACATTCTCG |
| | | Glutathione peroxidase 2 | GPX2 | GAATGGGCAGAACGAGCATC | CCGGCCCTATGAGGAACTTC |
| | | Glutathione peroxidase 3 | GPX3 | GAGCTTGCACCATTCGGTCT | GGGTAGGAAGGATCTCTGAGTTC |
| | | Glutathione peroxidase 4 | GPX4 | GAGGCAAGACCGAAGTAAACTAC | CCGAACTGGTTACACGGGAA |
| | | Glutathione peroxidase 5 | GPX5 | ATGACTACACAGTTAAGGGTCGT | GGATATTGCGCTGTCAGACCA |
| | | Glutathione peroxidase 6 | GPX6 | CAAAGGGGTAACAGGCACCAT | GGCGGCCACATTGACAAAC |
| | | Glutathione peroxidase 7 | GPX7 | CGCACCTACAGTGTCTCATTC | CAGGTAGTTGAAGGCAGGATG |
| | | Glutathione-disulfide reductase | GSR | CACTTGCGTGAATGTTGGATG | TGGGATCACTCGTGAAGGCT |
| | | Glutathione synthetase | GSS | GGAACATCCATGTGATCCGAC | GCCATCCCGGAAGTAAACCA |
| | | Heme oxygenase 1 | HMOX1 | | |
| | | Homo sapiens heat shock protein family A (Hsp70) member 1 | HSPA1A | cgactgaacaagagcatca | aagactgcgcdgctggt |
| | Oxidative Stress Responsive Genes: | Keratin 1 | KRT1 | AGAGTGGACCAACTGAAGAGT | ATTCTCTGCCATTTGTCCGCTT |
| | | Lactoperoxidase | LPO | CTCTTTCTCCGCGAGCATAAC | AATGGGTAGGTAGTCCCTAAAGG |
| | | Mannose binding lectin 2 | MBL2 | CCCTGTTTCCATCACTCCCTC | GCAGGTCTTTTGGGCATCC |
| | | Myeloperoxidase | MPO | CCAGATCATCACTTACCGGGA | CACTGAGTCATTGTAGGAACGG |
| | | Methionine sulfoxide reductase A | MSRA | GGCCATCTACCCGACCTCT | GCCATTGGGGTTCTTGCTCA |
| | | NAD(P)H quinone dehydrogenase 1 | NQO1 | GAAGAGGCACTGATCGTACTGGC | GGATACTGAAAGTTCGCAGGG |
| | | Nudix hydrolase 1 | NUDT1 | GCTCATGGACGTGCATGTCTT | GTGGAAACCAGTAGCTGTCAT |
| | | Oxidation resistance 1 | OXR1 | TAGCATCTGAGCCACTGAAAGT | CACCACCGGAAAGCTAGTGAATC |
| | | Oxidative stress responsive kinase 1 | OXSR1 | AGGGACGATTACGAGCTGC | TCCGTTTGATTGCCACTTTCTC |
| | | PDZ and LIM domain 1 | PDLIM1 | GACACACTTGGAAGCTCAGAAC | GTAAAGGGCATGGCACTTCG |
| | | Polynucleotide kinase 3'-phosphatase | PNKP | CTGACCCAGGTTACGGACC | TCCCGGTAGTTGAGGGGTT |
| | | Peroxiredoxin 2 | PRDX2 | GAAGCTGTCGGACTACAAAGG | TCGGTGGGGCACACAAAAG |
| | | Peroxiredoxin 5 | PRDX5 | GCAAGACGGTGCAGTGAAG | ATGGCATCTCCCACCTTGATT |
| | | Peroxiredoxin 6 | PRDX6 | GACTCATGGGGCATTCTCTTC | CAAGCTCCCGATTCCTATCATC |
| | | Prion protein | PRNP | AGTCAGTGGAACAAGCCGAG | CTGCCGAAATGTATGATGGGC |
| | | Ring finger protein 7 | RNF7 | CGGGAGGCGACAAGATGTTC | TCCCCAGACCACAACACAGT |
| | | Scavenger receptor class A member 3 | SCARA3 | TCACCCAGGAGTGCTACGAT | GAGCCGTGTGTAGTTCTGCC |
| | | Selenoprotein P | SELENOP | GAAGAGCCTGCAGTAAAACTGA | ACAAGACGGCCACATCTATCATA |
| | | Sirtuin 2 | SIRT2 | CACGCAGAACATAGATACCCTG | CAGTGTGATGTGTAGAAGGTGC |
| | | superoxide dismutase 1 | SOD1 | | |
| | | superoxide dismutase 2 | SOD2 | | |
| | | Sequestosome 1 | SQSTM1 | GACTACGACTTGTGTAGCGTC | AGTGTCCGTGTTTCACCTTCC |
| | | Sulfiredoxin 1 | SRXN1 | CAGGGAGGTGACTACTTCTACTC | CAGGTACACCCTTAGGTCTGA |
| | | Serine/threonine kinase 25 | STK25 | GCTCCTACCTAAAGAGCACCA | TGGCAATGTATGTCTCCTCCAG |
| | | Thyroid peroxidase | TPO | CTGTCACGCTGGTTATGGC | GCTAGAGACAGAGACTCCTCA |
| | | Titin | TTN | CCCCATCGCCCATAAGACAC | CCACGTAGCCCTCTTGCTTC |
| | | Thioredoxin | TXN | GTGAAGCAGATCGAGAGCAAG | CGTGGCTGAGAAGTCAACTACTA |
| | | Thioredoxin reductase 1 | TXNRD1 | ATGGGCAATTTATTGGTCCTCAC | CCCAAGTAACGTGGTCTTTCAC |
| | | Thioredoxin reductase 2 | TXNRD2 | CGGCTTCGACCAGCAAATG | ACAGACGGTGTCAAAGGTG |
| | | Selenoprotein S | SELENOS | ACCTATGGCTGGTACATCGTC | GCCTCAAGGCTCTTAGCCC |
| Oxygen Transporters | | Cytoglobin | CYGB | CCCGGCTCTATGCCAACTG | CCATGTGCTTGAACTGGCTGA |
| | | Myoglobin | MB | TTGGTGCTGAACGTCTGGG | TGGGTGACCCTTAAAGAGCCT |

FIG. 10

SEQUENCE LISTING

```
<160> NUMBER OF SEQ ID NOS: 258

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
catcagaccg gcagattaac c                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gttggcctta cagcggtaga t                                              21

<210> SEQ ID NO 3
<211> LENGTH: 21
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtggctgacc tggtacaaga g                                            21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtagatgcg tctgagttcc at                                           22

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaggccaagc cctggtatg                                               19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgggccgatt gatctcagc                                               19

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acagttgcag ccgtagtctt g                                            21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccaggtcgtt gtgagcttct                                              20

<210> SEQ ID NO 9
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 9
tgaaaagctc cgggtcttag g                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttgactggcg tgatgtagtt g                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cttgggagac aacacgcatt t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tctcgctatt cccgacctct t                                              21

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cagcgacctt tccgtgtct                                                 19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggtctccaa tgctttggct                                                20

<210> SEQ ID NO 15
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 15
gaggttggct ctgactgtac c                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tccgtcccag tagattacca c                                              21

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgggccatgc ctgtttaca                                                 19

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tgtccttcgt tgaagtccct c                                              21

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gagtttgtcg ctcctgagat agt                                            23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcttagtgtc tccaagaaat ggg                                            23

<210> SEQ ID NO 21
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 21
tcccgcagag atactgactg t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggacccagaa cacacctact c                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtcatcgaac gcaccttcca t                                              21

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agcttcaggt actcaaactc gt                                             22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cccagagttt gagccgagtg                                                20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cccatccctt cgtcgtcct                                                 19

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
    primer

<400> SEQUENCE: 27
atggtcacct tacctctgca a                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tcatagcgtc ggttgatgtc g                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cccgagaggt cttttccga g                                               21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccagcccatg atggttctga t                                              21

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
taagttctga gtgtgaccga ga                                             22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gctctgtctg tagggaggta gg                                             22

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 33
atggaccgta gcatccctcc                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtaggtgcgt aggttctggt                                               20

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gacctggacc ctatggagga c                                             21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cctcagtctg gtcgtagatg a                                             21

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cagggctcct gggtagaact                                               20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctactccgtc cagactcatg c                                             21

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 39
ttggatgcac aacatgaatc agg                                          23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tcttctgact gagagctatg gtc                                          23

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
agaggtcata ggggttccac a                                            21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gctgacaacg gtgtttccat t                                            21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
attccggtga tacacgagca g                                            21

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gctggtgggt ctggtactc                                               19

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
```
tctggacacc cttgttgaat ct                                          22

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tggaaaaggt tcacaactgc tac                                         23

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggtggggtca tgtgtgtgg                                              19

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cggttcaggt actcagtcat cc                                          22

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tacaggctgg ctcaggacta t                                           21

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cgcaacattt tgtagcactc tg                                          22

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gagctggtgg ttgactttct c            21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tccatctccg attcagtccc t            21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gcggagttca cagctctata c            21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
aaaaggcccc tacagttacc a            21

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ttcctttagc tcctaacaca ggc           23

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tgctgctcca gtgatagacg a            21

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gttcagtggt tcttactcca gc           22

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
actgtagggg ttagtcctcg at                                              22

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tttccgtggc tcttattcaa act                                             23

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcacagtggt aggaacttct cat                                             23

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tagtgtatgc ctcgtttgtt gg                                              22

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ttctgtgtgt gctcaccttt c                                               21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tggctccctg gattatcaag a                                               21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ccagtgtcag gctaatgtct g                                              21

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tggggaacgg aactgatttt tc                                             22

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ttttgtggtg acttggggtt g                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gagcaacaac ttggtaaccc t                                              21

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggctggctat aaatggagct tg                                             22

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ggacctccag atgcttgttg a                                              21

```
<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggagctgctt ggactgacg                                                  19

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tctggttctt acgtctgttg c                                               21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ctgtgcagtc cctagctttc c                                               21

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
aggatattgg gctttacaac ctg                                             23

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gaggtaacag aggtcagcat ttt                                             23

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gtgcctttgt ggctaaacac t                                               21

<210> SEQ ID NO 76
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
agtcccgttt tgtccttacg a                                              21

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
aagggatttg ttgacataac ggg                                            23

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cagccgtagt tcttcgtaag c                                              21

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gaccgcagct atgaccctc                                                 19

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ctccggttca gcctctttag a                                              21

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tttccgcaag gttcgatttt ca                                             22

<210> SEQ ID NO 82
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ggcatctgcg ctctaccatc                                                   20

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
agaaacctgc tctacgaact gt                                                22

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gggaagcgag tctttcagaa g                                                 21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
accatgaaaa gagaccccac t                                                 21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gagtaccacg aaggcacaac t                                                 21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
agctgttgtt gagcgaattg t                                                 21

<210> SEQ ID NO 88
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 88
agcaagttga ggagttccac a                                             21

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gaaattgtgg aattgatgcg tga                                           23

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ctacaacgat ccctctgaa aaa                                            23

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
caagagaagc aacgtatggc a                                             21

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
aggcagatgg tcaaactctg ta                                            22

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ttcaacacca cataacgtgt cc                                            22

<210> SEQ ID NO 94
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 94
gtcaaggttg ctcgttctat gg                                                  22

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
caccaacata actgaggtgg atg                                                 23

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
aggaggagcc atattttccc a                                                   21

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
agtgacaggt atgggcgttc                                                     20

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
cggcatttgt atggtcctct t                                                   21

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tcatggacca cagtaacatg ga                                                  22

<210> SEQ ID NO 100
<211> LENGTH: 23
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 100
agtgaactga gatgtcagct cat                                          23

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
ctcagaccag agattcgcaa ac                                           22

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gcatttcccc tcaaactctc aa                                           22

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
aggagcaggg acaagttaca g                                            21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
ggacaatggg catagggtgt t                                            21

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
tggatgctct gtacgggaag                                              20

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
ccaggctggt gtgaaactga a                                        21

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ttccagcgat ggcatgttcc                                          20

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tcctactgtt gataagccca ca                                       22

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
aaggtggagt accacagagg                                          20

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tccatgtatg gtgacccatc c                                        21

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gccaggttac ggcagattca                                          20

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gaaggtcacg agcgtcacc                                              19

<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
actgaaaagc aatcgggaac tt                                          22

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cacacacaat ctccgcatct t                                           21

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
cagagaggca ctactgggct                                             20

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
cggtatgcaa ggatcacact g                                           21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
aatagtgcca cgcagtctac a                                           21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 118
cagatggcct gtctaaggca a                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
ggtgggccaa aggatgaaga g                                              21

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
ccacaagcca aacgacttcc                                                20

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ggaagccatc aaacgtgact t                                              21

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
cccgttcctt attgaaacca agc                                            23

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
atgctggcgc tactgtgttc                                                20

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
```

-continued ctccgccgag tcagagttg                                              19

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
atggccctca aacgtgttta c                                           21

<210> SEQ ID NO 126
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gcactggcga accttctca                                              19

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
atcgagggaa ctattgacgg c                                           21

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
agttgtttgt aaggtccccg ta                                          22

<210> SEQ ID NO 129
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
gagaccccat gttcgaccc                                              19

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ggaatgcgag gaaccataga tg                                                  22

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
acggtgtgta tcaggctctg                                                     20

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cacgtcggaa agaacatggt ag                                                  22

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
acctcctgca agaagagctg                                                     20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
ctatctccac gtgctccaca                                                     20

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ggggcgatca atccagagaa c                                                   21

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gtactcggta agtgtgccct g                                                   21

<210> SEQ ID NO 137
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 137
ccagaagcat taaccgagac aa                                              22

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 138
cctcgaagct gaatcaaggc                                                 20

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 139
ttcagtatca caacctcagc aag                                             23

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 140
tggacctgca agttaaaatc cc                                              22

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 141
cagatgttgg ggctaggatt g                                               21

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 142
gagtgttcgg cacatgggta                                                 20

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
actcagcagt ttaagaccat tgc                                              23

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ggactctttc acatgcagag c                                                21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ggaggtggtc ggagatacca a                                                21

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
acaatggcat tacgagcaac at                                               22

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
atgcctgtct gattcccatc t                                                21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
catgacactt ggcaatcctc t                                                21

```
<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
tgagtctgga cggagtagct c                                               21

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ccctgttggt atcttgtggt gt                                              22

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gacatcgggg ctaatctgaa g                                               21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ggctttactg tcacgtaccc a                                               21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
ctttgccccg tgttttctag g                                               21

<210> SEQ ID NO 154
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
ggataatccc gctgtagttt gg                                              22

<210> SEQ ID NO 155
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
ccttacaggg acaagtacag ca                                                22

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
ctgtgcctcc gtaaatggtt t                                                 21

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
gttgctggtc acattcctgg                                                   20

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gcaggtaatc ccaaaagcga c                                                 21

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gtgctgaagc tgtctctcgg                                                   20

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
gcccaaggta ggaaacagtc ttt                                               23

<210> SEQ ID NO 161
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
tggagctggt aacccagtag g                                              21

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
cctttgcctt ggagtatttg gta                                            23

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ccagcagtcg tctttgtcac                                                20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
ctctgggttg gcacacactt                                                20

<210> SEQ ID NO 165
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
cccggctcta tgccaactg                                                 19

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ccatgtgctt gaactggctg a                                              21

<210> SEQ ID NO 167
<211> LENGTH: 21
<212> TYPE: DNA
```

-continued

<213> ORGANISM: Artificial Sequence
<220> FEATURE:
<223> OTHER INFORMATION: Description of Artificial Sequence: Synthetic
      primer

<400> SEQUENCE: 167
cactgtctca ctacgtgtcg g                                              21

<210> SEQ ID NO 168
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
ccagccaatg gaggtcagc                                                 19

<210> SEQ ID NO 169
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gccttgctta ccttatgagg ac                                             22

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gggagagatg atgcttcgcc                                                20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
ccaaccagat tgtgcgcttc                                                20

<210> SEQ ID NO 172
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
cgcaggtcct ctcacagtc                                                 19

<210> SEQ ID NO 173
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 173
atacgtggat tgaggaccac t                                              21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
tccaatgtca agtagcggtt g                                              21

<210> SEQ ID NO 175
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
tcctacgttt acctgtccat gt                                             22

<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gtttgtgcag ttccagtagt ga                                             22

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ggcacaagga cgttctcaag t                                              21

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
cagacaggac caaccggac                                                 19

<210> SEQ ID NO 179
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 179
tgtcttggaa tgcactgtat ctc                                              23

<210> SEQ ID NO 180
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
cccagtaagg ctgtaaatgc tc                                               22

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
cagtcggtgt atgccttctc g                                                21

<210> SEQ ID NO 182
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
gagggacgcc acattctcg                                                   19

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
gaatgggcag aacgagcatc                                                  20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ccggccctat gaggaacttc                                                  20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
                                primer

<400> SEQUENCE: 185
gagcttgcac cattcggtct                                                  20

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gggtaggaag gatctctgag ttc                                              23

<210> SEQ ID NO 187
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
gaggcaagac cgaagtaaac tac                                              23

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ccgaactggt tacacgggaa                                                  20

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
atgactacac agttaagggt cgt                                              23

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
ggatattgcg ctgtcagacc a                                                21

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 191
caaaggggta acaggcacca t                                              21

<210> SEQ ID NO 192
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
ggcggccaca ttgacaaac                                                 19

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
cgcacctaca gtgtctcatt c                                              21

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
caggtacttg aaggcaggat g                                              21

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
cacttgcgtg aatgttggat g                                              21

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
tgggatcact cgtgaaggct                                                20

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 197
ggaacatcca tgtgatccga c                                              21

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
gccatcccgg aagtaaacca                                                20

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
cgacctgaac aagagcatca                                                20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
aagatctgcg tctgcttggt                                                20

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
agagtggacc aactgaagag t                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
attctctgca tttgtccgct t                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
```
ctctttctcc gcgagcataa c                                             21

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
aatgggtagg tagtccctaa agg                                           23

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
ccctgtttcc atcactccct c                                             21

<210> SEQ ID NO 206
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
gcaggtcttt tgggcatcc                                                19

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
ccagatcatc acttaccggg a                                             21

<210> SEQ ID NO 208
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
cactgagtca ttgtaggaac gg                                            22

<210> SEQ ID NO 209
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
ggccatctac ccgacctct					19

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 210
gccattgggg ttcttgctca					20

<210> SEQ ID NO 211
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 211
gaagagcact gatcgtactg gc				22

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 212
ggatactgaa agttcgcagg g					21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 213
gctcatggac gtgcatgtct t					21

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 214
gtggaaacca gtagctgtcg t					21

<210> SEQ ID NO 215
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 215
tagcatctga gccactgaaa gt				22

<210> SEQ ID NO 216
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
caccaccgaa agctagtgaa tc                                              22

<210> SEQ ID NO 217
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
agggacgatt acgagctgc                                                  19

<210> SEQ ID NO 218
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
tccgtttgat tgccactttc tc                                              22

<210> SEQ ID NO 219
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
gacacacttg gaagctcaga ac                                              22

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
gtaaagggca tggcacttcg                                                 20

<210> SEQ ID NO 221
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
ctgacccagg ttacggacc                                                  19

<210> SEQ ID NO 222
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
tcccggtagt tgaggggtt                                              19

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gaagctgtcg gactacaaag g                                           21

<210> SEQ ID NO 224
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
tcggtggggc acacaaaag                                              19

<210> SEQ ID NO 225
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
gcaagacggt gcagtgaag                                              19

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
atggcatctc ccaccttgat t                                           21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
gactcatggg gcattctctt c                                           21

```
<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
caagctcccg attcctatca tc                                              22

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
agtcagtgga acaagccgag                                                 20

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
ctgccgaaat gtatgatggg c                                               21

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
cgggaggcga caagatgttc                                                 20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
tccccagacc acaacacagt                                                 20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
tcacccagga gtgctacgat                                                 20

<210> SEQ ID NO 234
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
gagccgtgtg tagttctgcc                                                   20

<210> SEQ ID NO 235
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
gaagacctgc gagtaaaact ga                                                22

<210> SEQ ID NO 236
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
acaagacggc cacatctatc ata                                               23

<210> SEQ ID NO 237
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
cacgcagaac atagataccc tg                                                22

<210> SEQ ID NO 238
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
cagtgtgatg tgtagaaggt gc                                                22

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
gactacgact tgtgtagcgt c                                                 21

<210> SEQ ID NO 240
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
agtgtccgtg tttcaccttc c                                              21

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
cagggaggtg actacttcta ctc                                            23

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
caggtacacc cttaggtctg a                                              21

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
gctcctacct aaagagcacc a                                              21

<210> SEQ ID NO 244
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
tggcaatgta tgtctcctcc ag                                             22

<210> SEQ ID NO 245
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
ctgtcacgct ggttatggc                                                 19

<210> SEQ ID NO 246
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 246
gctagagaca cgagactcct ca                                               22

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
ccccatcgcc cataagacac                                                  20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
ccacgtagcc ctcttgcttc                                                  20

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
gtgaagcaga tcgagagcaa g                                                21

<210> SEQ ID NO 250
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
cgtggctgag aagtcaacta cta                                              23

<210> SEQ ID NO 251
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
atgggcaatt tattggtcct cac                                              23

<210> SEQ ID NO 252
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 252
cccaagtaac gtggtctttc ac                                              22

<210> SEQ ID NO 253
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
cggcttcgac cagcaaatg                                                  19

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
acaggacggt gtcaaaggtg                                                 20

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
acctatggct ggtacatcgt c                                               21

<210> SEQ ID NO 256
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
gcctcaaggc tcttagccg                                                  19

<210> SEQ ID NO 257
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
ttggtgctga acgtctggg                                                  19

<210> SEQ ID NO 258
<211> LENGTH: 21
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 258
tgggtgaccc ttaaagagcc t                                              21
```

METHOD FOR TREATMENT OF CANCER WITH COMBINATION OF COLD ATMOSPHERIC PLASMA AND A GENE INHIBITOR

CROSS-REFERENCE TO RELATED APPLICATIONS

The present application claims the benefit of the filing date of U.S. Provisional Patent Application Ser. No. 62/953,754 filed by the present inventors on Dec. 26, 2019.

The aforementioned provisional patent application is hereby incorporated by reference in its entirety.

STATEMENT REGARDING FEDERALLY SPONSORED RESEARCH OR DEVELOPMENT

None.

SEQUENCE LISTING

The instant application contains a Sequence Listing which has been submitted electronically in ASCII format and is hereby incorporated by reference in its entirety. Said ASCII copy, created on Feb. 26, 2021, is named 9101_115_SL.txt and is 59,010 bytes in size.

BACKGROUND OF THE INVENTION

Field of the Invention

The present invention relates to systems and methods for treating cancer with cold atmospheric plasma.

Brief Description of the Related Art

Breast cancer is the most common cause of cancer death among women worldwide (F. Bray, J. Ferlay, I. Soerjomataram, R. L. Siegel, L. A. Torre, A. Jemal, "Global cancer statistics 2018: GLOBOCAN estimates of incidence and mortality worldwide for 36 cancers in 185 countries," CA Cancer J Clin, 68 (2018) 394-424) and it exhibit diverse molecular features that reflect the high heterogeneity which complicates the clinical treatment (N. Howlader, K. A. Cronin, A. W. Kurian, R. Andridge, "Differences in Breast Cancer Survival by Molecular Subtypes in the United States," Cancer Epidemiol Biomarkers Prey, 27 (2018) 619-626). Breast cancer are categorized by the molecular receptor status that are expressed such as the estrogen receptor (ER), progesterone receptor (PR) and human epidermal growth factor receptor 2 (HER2) expression. Prognosis for breast cancer patients is generally favorable with ER+/PR+ tumors, intermediate with either ER+/PR− or ER−/PR+ tumors, and usually poor for ER−/PR− tumors. Based on the receptor status selective therapeutic interventions are carried out. For example, in the case of ER+ tumor estrogen-receptor modulators, such as Tamoxifen and letrozole are administered, trastuzumab is (Herceptin), a humanized monoclonal antibody developed to target and inhibit the function of HER2 and a dual anti-HER2 regimen, pertuzumab in combination with trastuzumab and docetaxel are administered to mitigate the risk of mortality to considerable effect, however the incidences of adverse events and resistance to these drugs are not uncommon. Triple negative breast cancer (TNBC) (ER−/PR−, HER2−) do not respond to endocrine therapy or HER2-targeted therapies. Therapies targeting TRAIL (TNF (tumor necrosis factor)-related apoptosis-inducing ligand) and cyclin dependent kinases (CDK) or cell cycle regulators have been used with limited success. In recent years Cold atmospheric plasma (CAP) technology that utilizes ionized gas to selectively induce apoptosis in cancer cells have shown very encouraging results. Preclinical In vivo studies in mouse models for various cancers for CAP treatment have demonstrated to effectively reduce tumor growth rate and induce cancer cell death. CAP treatment induces apoptosis in various breast cancer cells and the potency of the treatment depend on a combination of parameters such as the concentration and the time of the plasma treatment. Susceptibility or resistance to CAP treatment is also determined by the molecular features of the cell types such as the receptor status which are classified into intrinsic subtypes including luminal A (ER+PR+/−HER2−), luminal B (ER+PR+/−HER2+), basal-like (ER−PR−HER2−), and HER2-positive (ER−PR−HER2+). At high concentrations and duration of CAP treatment most of the breast cancer cells often undergo apoptosis due to the release of reactive oxygen and nitrogen species (RONS) and oxidative stress-induced cell toxicity of these species. The mechanism of such oxidative stress-induced cell death process is broadly discussed in various studies. CAP treatment on subtypes of breast cancer cell lines has been demonstrated to reduce breast cancer viability by 92-99% regardless of the status of the receptors on these cells at the most optimal power setting and time of treatment. However, some subset of cells resists the CAP insult and survive, but the molecular mechanism for such survival in these cells has not been systematically investigated.

Several different systems and methods for performing Cold Atmospheric Plasma (CAP) treatment have been disclosed. For example, U.S. Pat. No. 10,213,614 discloses a two-electrode system for CAP treatement. U.S. Pat. No. 9,999,462 and U.S. Pat. No. 10,023,858 each disclose a converter unit for using a traditional electrosurgical system with a single electrode CAP accessory to perform CAP treatment. WO 2018191265A1 disclosed an integrated electrosurgical generator and gas control module for performing CAP.

SUMMARY OF THE INVENTION

Breast cancer is the leading cause of cancer death among women. Predominantly, the poor prognosis is due to the triple-negative breast cancer characterized by the absence or low-level expression of estrogen (ER), progesterone (ER), and HER2 receptors. Cold atmospheric plasma (CAP) jet delivered by the Canady Cold Plasma Conversion system that induces cell death in triple-negative breast cancer cell line without thermal damage, however, the mechanism of cell death by CAP treatment is ambiguous. In this study, we aimed to investigate the gene expression profile by screening the expressions of apoptotic and oxidative stress related gene markers in breast cancer cell lines after CAP treatment to determine the molecular mechanism of CAP induced cell death. Six different types of breast cancer cell lines including MCF-7 and T-47D (luminal A: ER+PR+/−HER2−), BT-474 (luminal B: ER+PR+/−HER2+), SK-BR-3 (ER−PR−HER2+), MDA-MB-231 and Hs578T (basal-like: ER−PR−HER2−) were tested with Canady Helios Cold Plasma Scalpel (CHCPS) with 2 power settings (80 p and 120 p, which are approximately 15 W, and 28 W respectively). Gene expression of 48 apoptotic and 35 oxidative gene markers were determined at 4 different time points (3 hrs, 6 hrs 12 hrs and 24 hrs) after treatment with CHCPS, using quantitative real time polymerase chain reaction (qRT-PCR).

After CAP treatment, the expression level of BCL2A1 and TNF were significantly increased in triple-negative cell lines, MDA-MB-231 and Hs578T (p<0.01). In contrast, the HER2-positive and ER, PR positive cell lines showed little or no expression of BCL2A1 (p<0.01). Silencing BCL2A1 mRNA by siRNA increased the potency of the CAP treatment. Combination of CAP and CPI203, a BET bromodomain inhibitor dramatic increased the CAP-induced cell death without any cytotoxicity by itself (p<0.05). Our results revealed that BCL2A1, act as potential key gene in breast cancer survival, thereby improving our understanding of molecular profiles of CAP induced cell death. The upregulation of BCL2A1 mRNA levels and expression of protein only after CAP induction in triple negative subtype could correspond an important molecular mechanism for their poor prognostic significance which could be reversed with a combination of siRNA or BCL2A1 antagonist-CAP therapy.

In a preferred embodiment, the present invention is a method for treatment of cancer. The method comprises treating a patient having a cancerous tumor with a gene inhibitor pre-operatively to inhibit upregulation of a particular gene, surgically removing the cancerous tumor, treating the patient with the gene inhibitor intra-operatively to inhibit upregulation of a particular gene, applying cold atmospheric plasma to surgical margins around the area in the patient from which the tumor was surgically removed, and treating the patient with the gene inhibitor post-operatively. The cancer may be triple negative breast cancer and the particular survival gene may be BCL2A1. The gene inhibitor may be CPI203. The pre-operative treatment of a patient with a gene inhibitor is within 24 hours of surgical removal of the cancerous tumor. The post-operative treatment of a patient with a gene inhibitor is within 24 hours after surgical removal of the cancerous tumor.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which:

FIG. 6B is an assembly view of a cable harness of a cold atmospheric plasma probe that may be used in a preferred embodiment of the present invention.

FIG. 7 (Table 1) is a table of genes selected based on their ability in "induction of apoptosis." Table 1 discloses SEQ ID NO. 1-22, respectively, in order of appearance.

FIG. 8 (Table 2) is a table of genes selected based on their ability in "regulation of apoptosis." Table 2 discloses SEQ ID NOS. 9-10, 23-68, 11-12, and 69-80, respectively, in order of appearance.

FIG. 9 (Table 3) is a table of genes selected based on their ability as "caspases & regulators." Table 3 discloses SEQ ID NOS. 81-188, respectively, in order of appearance.

FIG. 10 (Table 4) is a table of genes selected based on their ability as "responders of oxidative stress." Table 4 discloses SEQ ID NOS. 119-256, 165-166, and 257-258, respectively, in order of appearance.

DETAILED DESCRIPTION OF THE PREFERRED EMBODIMENTS

Breast cancer is the leading cause of cancer death among women. Predominantly, the poor prognosis is due to the triple-negative breast cancer characterized by the absence or low-level expression of estrogen (ER), progesterone (ER), and HER2 receptors. Cold atmospheric plasma (CAP) delivered to cancer cells induces cell death in triple-negative breast cancer cell line without thermal damage. The present inventors investigated the gene expression profile when CAP is applied by screening the expressions of apoptotic and oxidative stress related gene markers in breast cancer cell lines after CAP treatment to determine the molecular mechanism of CAP induced cell death. Six different types of breast cancer cell lines including MCF-7 and T-47D (luminal A: $ER^+PR^{+/-}HER2^-$), BT-474 (luminal B: $ERVR^{+/-}HER2^+$), SK-BR-3 ($ER^-PR^-HER2^+$), MDA-MB-231 and Hs578T (basal-like: $ER^-PR^-HER2^-$) were tested with CAP at two power settings (80 p and 120 p, which are approximately 15 W, and 28 W respectively). Gene expression of 48 apoptotic and 35 oxidative gene markers were determined at four different time points (3 hrs, 6 hrs 12 hrs and 24 hrs) after treatment with CAP, using quantitative real-time polymerase chain reaction (qRT-PCR). After CAP treatment, the expression level of BCL2A1 and TNF were significantly increased in triple-negative cell lines, MDA-MB-231 and Hs578T ($p<0.01$). In contrast, the HER2-positive and ER, PR positive cell lines showed little or no expression of BCL2A1 ($p<0.01$). Silencing or inhibiting BCL2A1 mRNA by siRNA increased the potency of the CAP treatment. Combination of CAP and CPI203, a BET bromodomain inhibitor, dramatically increased the CAP-induced cell death without any cytotoxicity by itself ($p<0.05$). The BCL2A1 expression is induced after CAP treatment, and BCL2A1, acts as potential key gene in breast cancer survival, thereby improving our understanding of molecular profiles of CAP induced cell death. The upregulation of BCL2A1 mRNA levels and expression of protein only after CAP application in the triple-negative subtype could correspond to an important molecular mechanism for their poor prognostic significance which could be reversed with a combination of siRNA or BCL2A1 antagonist-immuno-CAP therapy.

Figure 1:
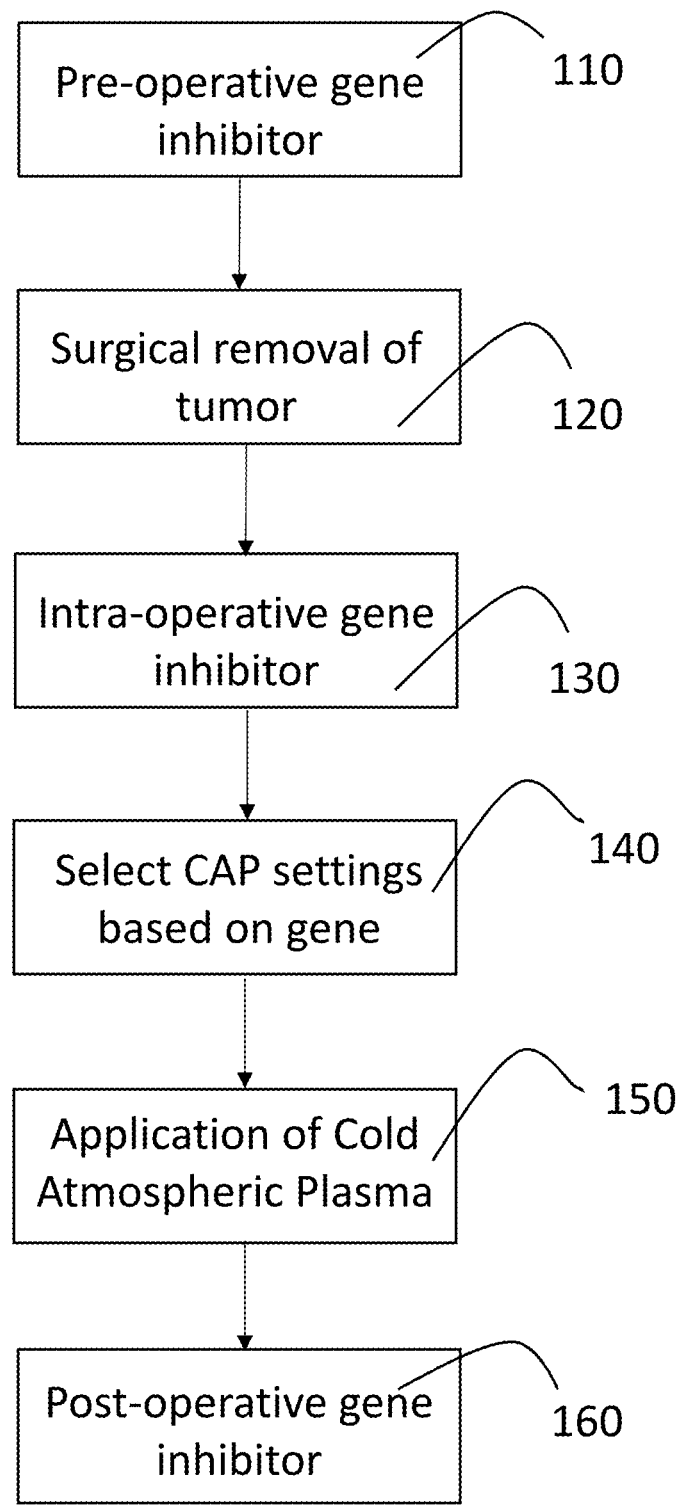
FIG. 1 is a flow diagram illustrating a method in accordance with a preferred embodiment of the present invention.

A method for treating breast cancer in accordance with a preferred embodiment of the present invention is shown in FIG. 1. The patient is given a gene inhibitor to inhibit an identified "survival gene" pre-operatively (neoadjuvant) to inhibit the identified gene (110). For triple negative breast cancer, the survival gene is BCL2A1. The pre-operative treatment may be, for example, 24 hours prior to surgery. For triple negative breast cancer, the gene inhibitor may be CPI203, a BET bromodomain inhibitor that inhibits upregulation of BCL2A1. The cancerous tumor is then surgically removed (120). The surgical removal may be via open surgery, robotic surgery, laparoscopic surgery, endoscopic surgery, or any other type of surgery. The gene inhibitor is given to the patient again intra-operatively (130). CAP settings are selected by the CAP system based upon the particular survival gene involved (140). For BCL2A1, the selected setting may be 80 p (15W). Cold plasma is then applied to the margins of the area from which the cancerous tumor was removed (150). The gene inhibitor is then given to the patient again post-operatively (adjuvant) (160), for example 24 hours after surgery.

Figure 2:
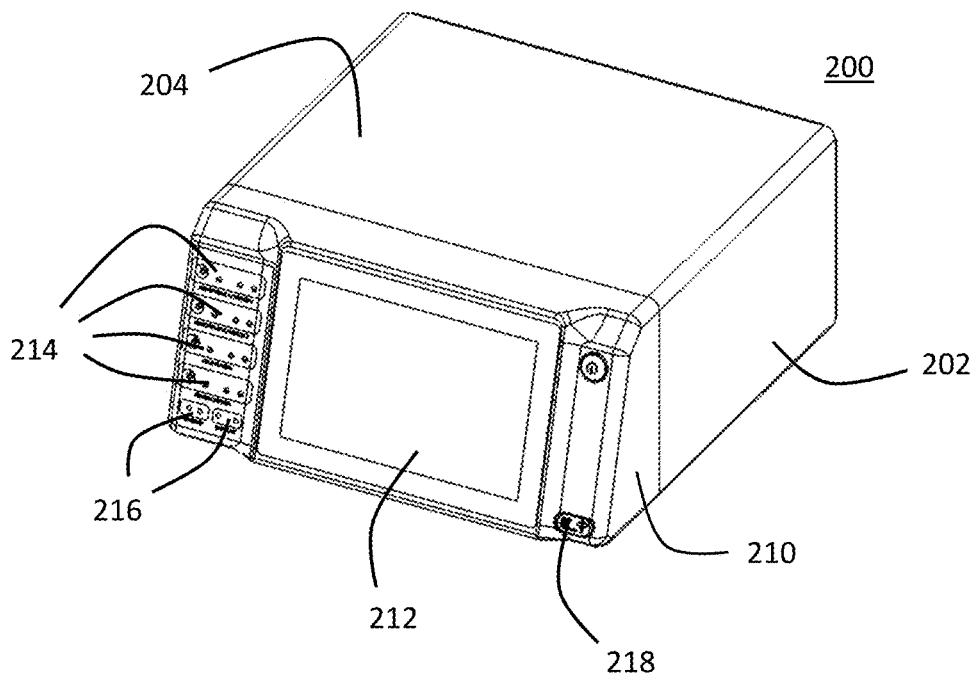
FIG. 2 is a perspective view of a preferred embodiment of a gas-enhanced electrosurgical generator that may be used in a preferred embodiment of the present invention.
Figure 3:
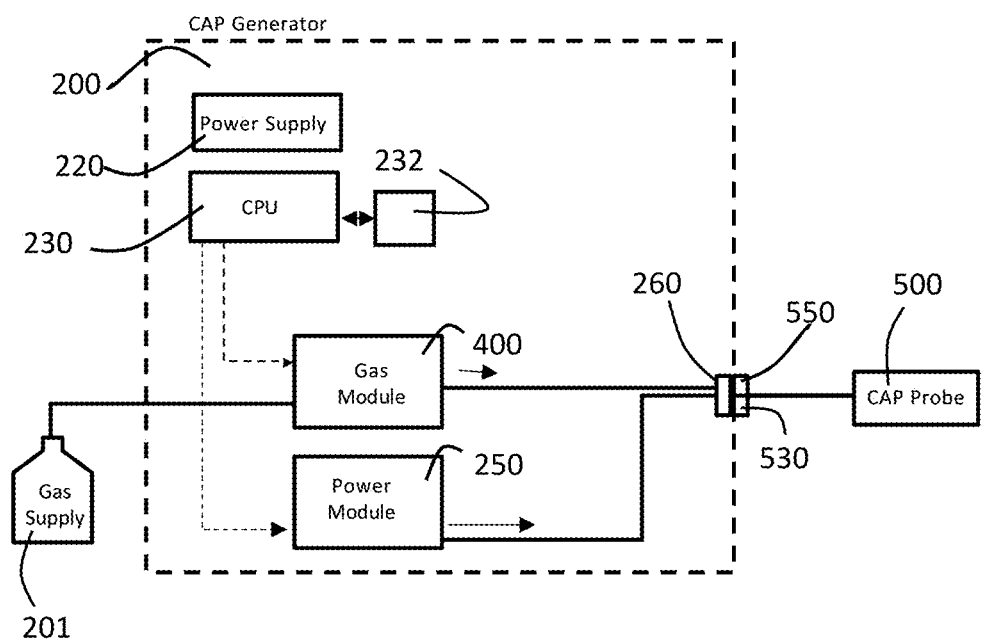
FIG. 3 is a block diagram of a cold atmospheric plasma generator in accordance with a preferred embodiment of the present invention.

A preferred embodiment of a CAP enabled generator is described with reference to the drawings. A gas-enhanced electrosurgical generator 200 in accordance with a preferred embodiment of the present invention is shown in FIGS. 2 and 3. The gas-enhanced generator has a housing 202 made of a sturdy material such as plastic or metal similar to materials used for housings of conventional electrosurgical generators. The housing 202 has a removable cover 204. The housing 202 and cover 204 have means, such as screws, tongue and groove, or other structure for removably securing the cover to the housing. The cover 204 may comprise just the top of the housing or multiple sides, such as the top, right side and left side, of the housing 202. The housing 202 may have a plurality of feet or legs (not shown) attached to the bottom of the housing. The bottom of the housing 202 may have a plurality of vents (not shown) for venting from the interior of the gas-enhanced generator.

A generator housing front panel 210 is connected to the housing 202. On the face front panel 210 there is a touch-screen display 212 and there may be one or a plurality of connectors 214 for connecting various accessories to the generator 200. For a cold atmospheric plasma generator such as is shown in FIG. 3, for example, there is a connector 260 for connecting a cold atmospheric probe 500. An integrated multi-function electrosurgical generator, such as is shown in FIG. 4B the plurality of connectors may include an argon plasma probe, a hybrid plasma probe, a cold atmospheric plasma probe, or any other electrosurgical attachment. The face of the front panel 210 is at an angle other than 90 degrees with respect to the top and bottom of the housing to provide for easier viewing and use of the touch screen display 212 by a user.

Figure 5:
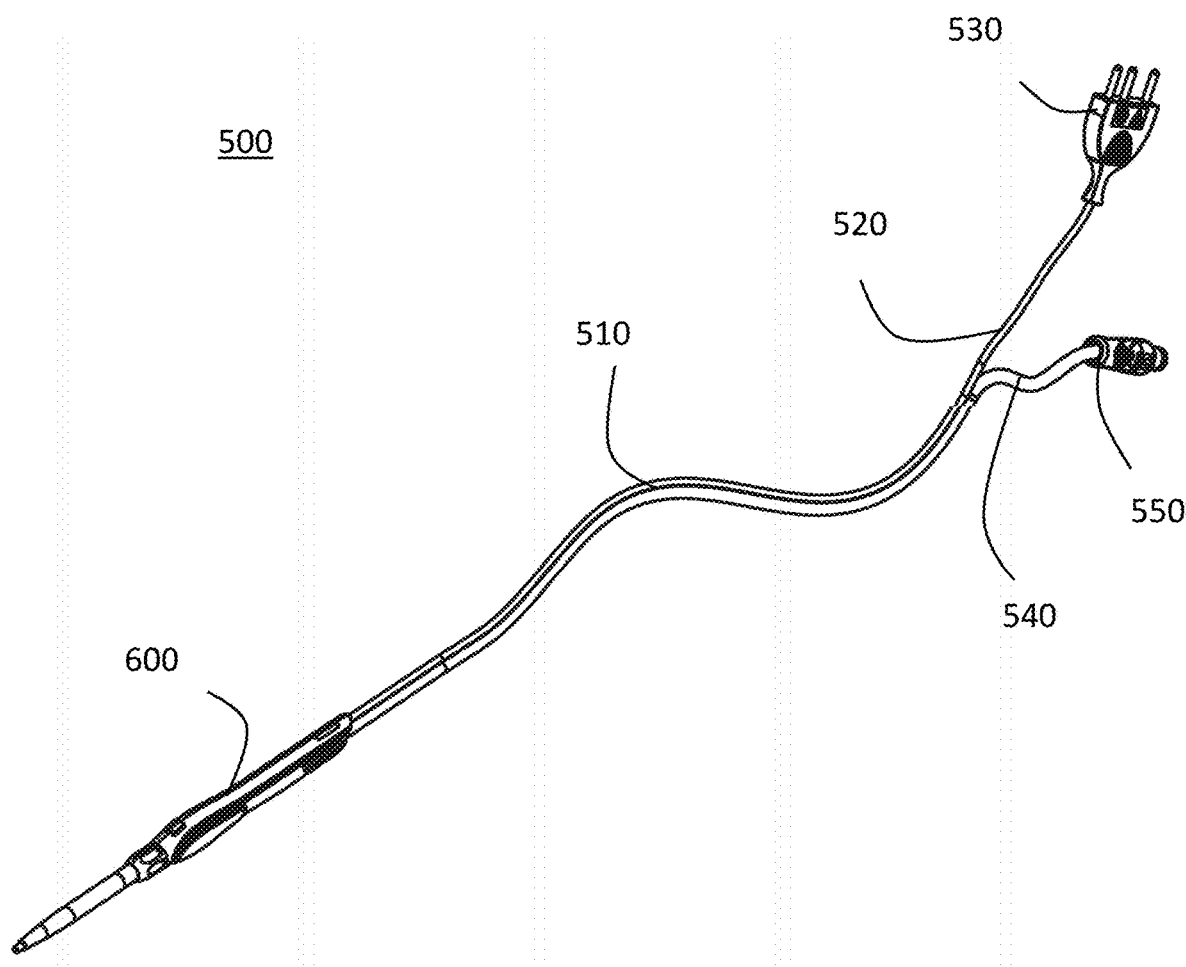
FIG. 5 is perspective view of a cold atmospheric plasma probe that may be used in a preferred embodiment of the present invention.
Figure 6A:
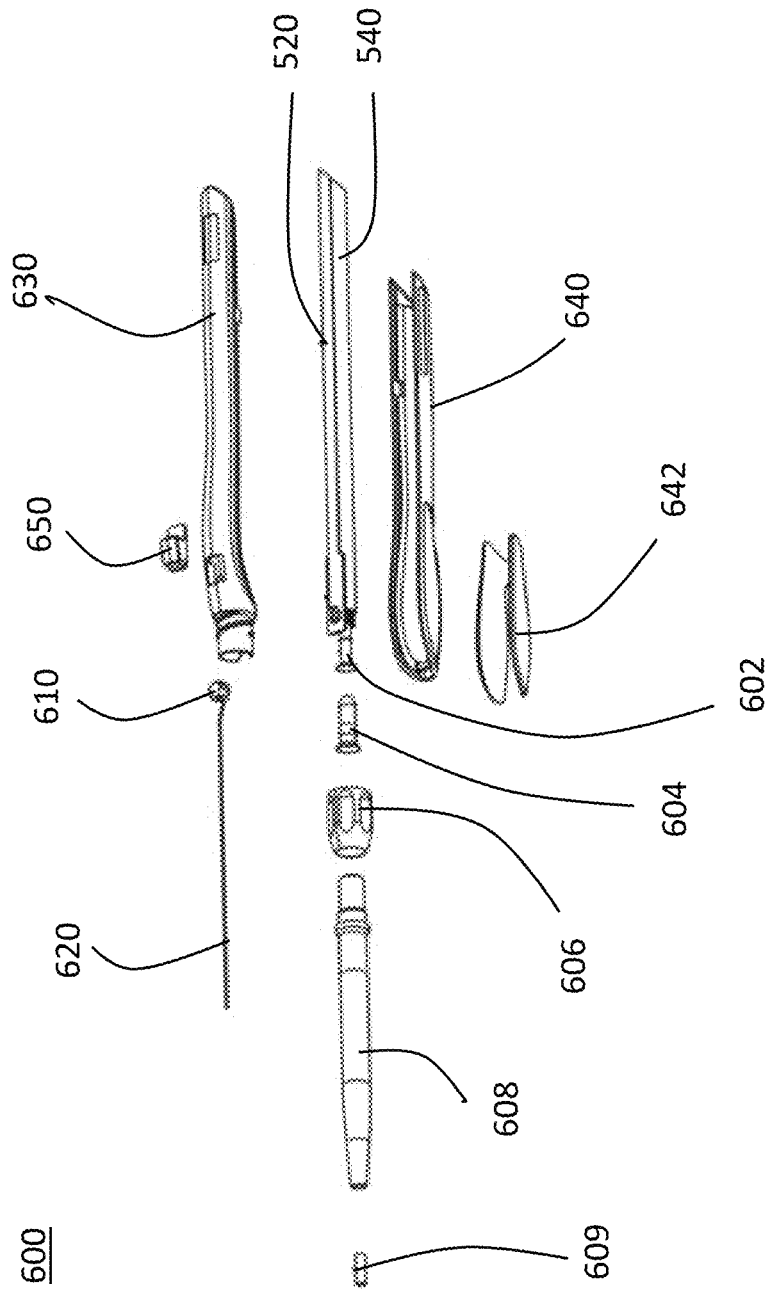
FIG. 6A is an assembly view of a handpiece of a cold atmospheric plasma probe that may be used in a preferred embodiment of the present invention.

As shown in FIG. 3, an exemplary cold atmospheric plasma (CAP) generator 200 has a power supply 220, a CPU (or processor or FPGA) 230 and a memory or storage 232. The system further has a display 212 (FIG. 2), which may be the display of a tablet computer. The CPU 230 controls the system and receives input from a user through a graphical user interface displayed on display 212. The CAP generator further has a gas control module 400 connected to a source 201 of a CAP carrier gas such as helium. The gas control module 400 may be, for example, of the design described in International Patent Application No. WO 2018/191265, which is hereby incorporated by reference. The CAP generator 200 further has a power module 250 for generating low frequency radio frequency (RF) energy, such as is described in U.S. Pat. No. 9,999,462, which is hereby incorporated by reference in its entirety. The power module 250 contains conventional electronics and/or transformers such as are known to provide RF power in electrosurgical generators. The power module 250 operates with a frequency between 10-200 kHz, which is referred to herein as a "low frequency," and output peak voltage from 3 kV to 6 kV and preferably at a frequency near (within 20%) of 40 Hz, 100 Hz or 200 Hz. The gas module 400 and power module 250 are connected to connector 260 that allows for attachment of a CAP applicator 500 (as shown in FIGS. 5, 6A and 6B) to be connected to the generator 200 via a connector having an electrical connector 530 and gas connector 550.

As shown in FIG. 4B, other arrangements for delivery of the carrier gas and the electrical energy may be used with the invention. In FIG. 4B, an integrated CAP generator 300b is connected to a source 310 of a carrier gas (helium in this example), which is provided to a gas control system 400, which supplies the gas at a controlled flow rate to CAP applicator 500. A high frequency (HF) power module 340b supplies high frequency (HF) energy to a low frequency power module (converter) 350b, which outputs electrical energy having a frequency in the range of 10 kHz to 200 kHz and an output voltage in the range of 3 kV to 6 Kv. This type of integrated generator will have both a CAP connector 360b for connecting a CAP applicator or other CAP accessory and a connector 370b for attaching HF electrosurgical attachments such as an argon plasma or hybrid plasma probe (not shown).

Figure 4A:
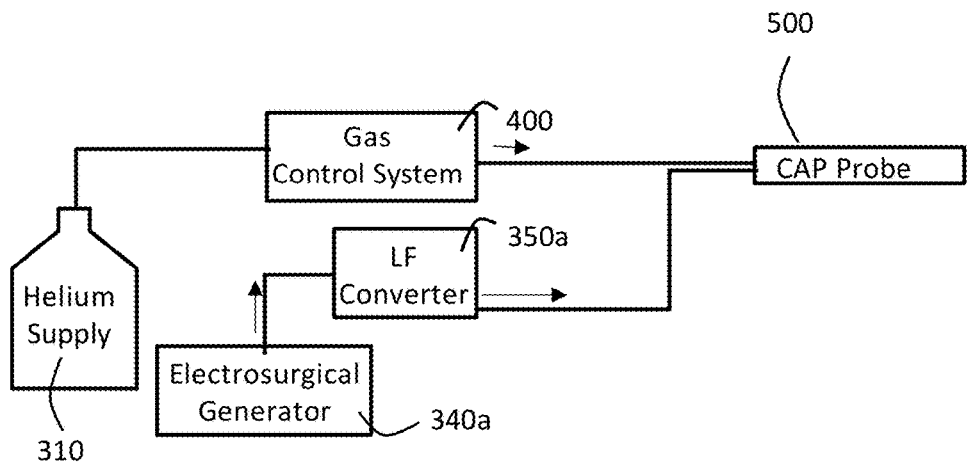
FIG. 4A is a block diagram of an embodiment of a cold atmospheric plasma system with an electrosurgical generator and a low frequency converter for producing cold plasma.
Figure 4B:
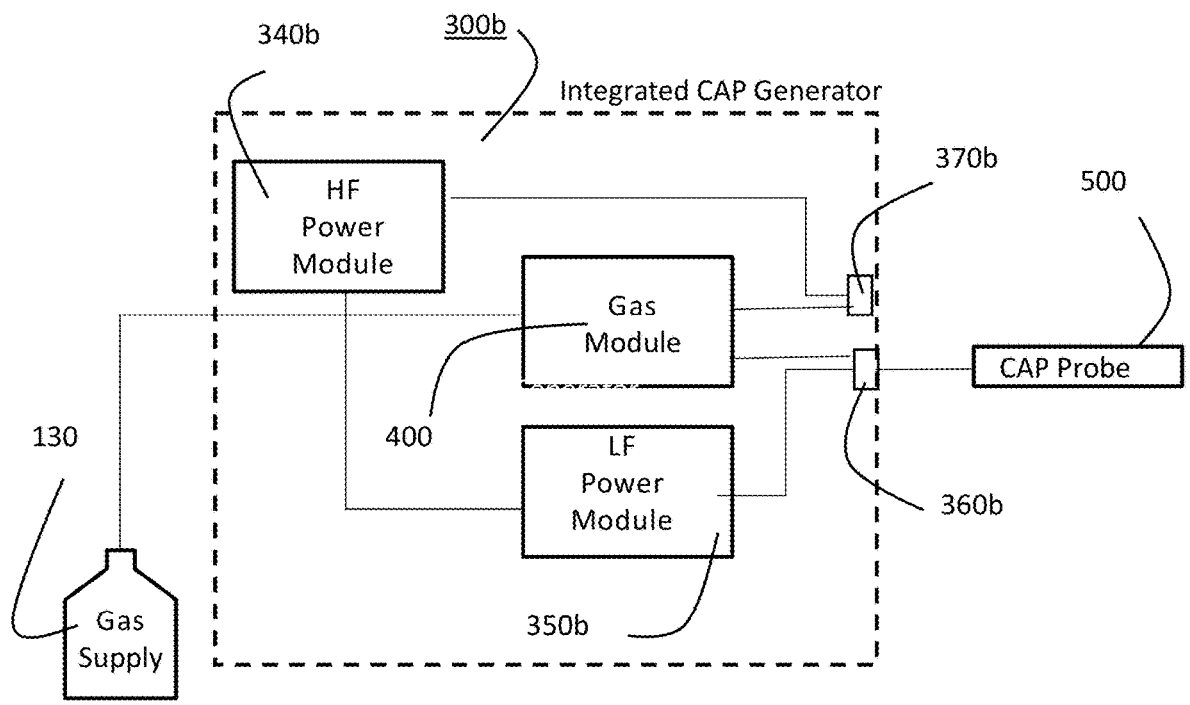
FIG. 4B is a block diagram of an embodiment of an integrated cold atmospheric plasma system that can perform multiple types of plasma surgeries.

Another embodiment, shown in FIG. 4A, has a carrier gas source 310 connected to a conventional gas control system 370, which in turn is connected to the CAP applicator 500, and a conventional electrosurgical generator 340 connected to a low frequency (LF) converter 350a, which is then connected to the CAP probe 500.

In the above-disclosed embodiment, a cold atmospheric plasma below 35° C. is produced. When applied to the tissue surrounding the surgical area, the cold atmospheric plasma induces metabolic suppression in only the tumor cells and enhances the response to the drugs that are injected into the patient.

The cold plasma applicator 500 may be in a form such as is disclosed in U.S. Pat. No. 10,405,913 and shown in FIGS. 5, 6A and 6B. A hand piece assembly 600 has a top side piece 630 and a bottom side piece 640. A control button 650 extends from the interior of the hand piece through an opening in the top side piece 630. Within the hand piece 600 is body connector funnel 602, PCB board 608, electrical wiring 520 and hose tubing (PVC medical grade) 540. The wiring 520 and hose tubing 540 are connected to one another to form a wire and tubing bundle 510. A grip over mold 642 extends over the bottom piece portion 640. In other embodiments, a grip may be attached to the bottom piece 640 in other manners. A probe or scalpel assembly is attached to the end of the hand piece. The probe assembly has non-bendable telescoping tubing 606, a ceramic tip 609, a column nut or collet 606 and body connector tubing 604. The hose tubing 540 extends out of the proximal end of the hand piece to a body gas connector 550, which has an O-ring 552, gas connector core 554 and gas connector tip 556 for connecting to a connector on a gas-enhanced electrosurgical generator. The printed circuit board 608 connects to electrical wiring 520 which leads to electrical connector 530 having electrical pins 532. Inside the handpiece 600 is an electrode 620 and conductive connector 610. There is a control button 650 for controlling the application of electrical energy.

Experiments
Materials and Methods:
Cold Plasma Device

A Cold Plasma System was used for performing all experiments at Jerome Canady Research Institute for Advanced Biological and Technological Sciences, Takoma Park, Md., USA. The electrosurgical device consists of the USMI SS-601 MCa high-frequency electrosurgical generator (USMI, Takoma Park, Md., USA) integrated with a USMI Canady Cold Plasma Conversion Unit and connected to a Canady Helios Cold Plasma™ Scalpel. The conversion unit has three connectors: a gas connector (to a helium tank), and electrical connector (to the generator), and an electro-gas connector (to the scalpel). The conversion unit also features a high voltage transformer that up-converts voltage up to 4 kV, down-converts frequency to less than 300 kHz, and down-converts power less than 40W. Additional details and schematics on plasma generation by CCPCS can be found in our previous study. The helium flow rate was set to a constant 3 L/min and the power was set to 80 and 120 P. The plasma scalpel tip was placed 1.5 cm above the surface of the cell media and remained unmoved for the duration of the treatment. The CAP treatment was performed in a laminar flow tissue culture hood, Purifier Logic+Class II, Type A2 Biosafety Cabinet (Labconco, Kansas City, Mo., USA) at room temperature.

Cell Culture

Human breast cancer cell lines T-47D, SK-BR-3, and BT-474, were purchased from ATCC (Manassas, Va., USA). MCF-7, MDA-MB-231, Hs578T, and HCC1806 were generously donated by Professor Kanaan's laboratory at Howard University. All cell lines except SK-BR-3 were cultured in Roswell Park Memorial Institute (RPMI) 1640 Medium supplemented with 10% fetal bovine serum (Sigma-Aldrich, St. Louis, Mo., USA) and 1% Pen Strep (Thermo Fisher Scientific, Waltham, Mass., USA) in a 37° C. and 5% CO2 humidified incubator (Thermo Fisher Scientific, Waltham, Mass., USA). The exceptions for culture conditions include T-47D, which was additionally supplemented with 0.5 mg/mL insulin. SK-BR-3 was cultured in McCoy's 5A Medium. When cells reached approximately 80% confluence, cells were seeded at a concentration of 105 cells/well into 12-well plates (USA Scientific, Ocala, Fla., USA) with a 1 mL media volume per well for cell viability assays.

Quantitative Real-Time RT-PCR

Total RNA was extracted from T-47D, SK-BR-3, BT-474, MCF-7, MDA-MB-231 and Hs578T cell pellets using the TRI reagent and Direct-sol MiniPrep kit (Zymo Research) with DNAse treatment according to the manufacturer's instructions. First-strand cDNA was synthesized with 1 μg of total RNA from these cells using Transcriptor First Strand cDNA Synthesis Kit (Roche Applied Science). Real-time RT-PCR reactions were performed according to the MIQE Guidelines (PMID: 19246619) Quantitative PCR was performed using 1uL (diluted 1:20 using PCR grade water) of first strand cDNA under the conditions of 95° C. for 15 seconds, annealing at 60° C. for 60 seconds, extension at 72° C. for 30 seconds for 40 cycles, and a final extension at 72° C. for 10 minutes using SYBR Green Master Mix (Applied Biosciences). Primer sequences for analyzing 18S RNA were used for normalization and relative mRNA expression were calculated with 2-ΔΔCT method. Primer sequences for all the 93 genes related to induction of apoptosis, regulation of apoptosis, caspases & regulators and responders of oxidative stress analyzed in this study are listed in Tables 1-4 in FIGS. 7-10.

Western Blotting

Protein lysates from cell pellets were prepared using RIPA buffer, supplemented with a complete protease inhibitor cocktail (Thermo Fisher Scientific, Waltham, Mass.) to prevent protein degradation. After centrifugation at 16,000 rcf for 20 min at 4 C, protein concentrations in the supernatants were determined using the Bio-Rad Protein Assay. Twenty grams of protein was denatured at 95° C. for 5 minutes, ran on 4-20% Mini-PROTEAN® TGX Stain-Free™ Protein gels (Bio-Rad), and then transferred onto Trans-Blot Turbo Mini 0.2 μm Nitrocellulose blots (Bio-Rad), according to standard protocols from Bio-Rad Laboratories (Hercules, Calif.) protocol (PMID: 23709336). After blocking with 5% nonfat milk at 4° C. for one hour, membranes were incubated overnight with gentle agitation at 4° C. in 30 ml of blocking buffer with a mixture containing anti-BCL2A1 a polyclonal antibody from Cell Signaling (Cell Signaling Technology, Inc., Danvers, Mass.) or Abcam at a 1:50 dilution. After washing the blots were incubated in goat anti-rabbit HRP Ab (Bio-Rad) (1:10000 dilution) in blocking buffer for 1 h with gentle agitation at room temperature. The blots were then incubation in Clarity western ECL substrate chemiluminescent detection reagent (Bio-Rad) for 5 min prior to imaging them on ChemiDoc MP imager (Bio-Rad). Protein band were analyzed by Band Analysis tools of ImageLab software version 4.1 (Bio-Rad) following standard protocol.

Transfection of siRNA

Human BCL2A1 targeting MISSION® esiRNA and matching scrambled control esiRNA were purchased from Sigma-Aldrich. Scrambled control esiRNA that does not target any gene was used as the negative control siRNA.

MDA-MB-231 cells were transfected with siRNA and transfection reagent according to the manufacturer's instructions. Transfection of BCL2A1 esiRNA or control esiRNA was done at 13 pmol. Briefly, cells were seeded in a 12-well-plate at a density of $1 \times 10^5$ cells/well overnight in (RPMI) 1640 Medium supplemented with 10% fetal bovine serum (Sigma-Aldrich, St. Louis, Mo., USA) and 1% Pen Strep (Thermo Fisher Scientific, Waltham, Mass., USA) in a 37° C. and 5% CO2 humidified incubator. The media was replaced with antibiotics-free medium RPMI 2 minutes before the transfection. esiRNA was mixed with Lipofectamine RNAiMAX transfection reagent in 100 µl optimal medium at the required concentration of 13 pmol/mL and were incubated at room temperature for 30 min to form a complex and the mixture was supplemented to each well with optimal medium. Four hours after the transfection, the transfected cells were CAP treated. After 24 hours after the CAP treatment, cells viability was assessed by using MTT assay.

Cell Viability Assay

Thiazolyl blue tetrazolium bromide (MTT) assay was performed on the cells 24 hours after plasma treatment following the manufacturer's protocol with all MTT assay reagents purchased from Sigma-Aldrich (St. Louis, Mo., USA). The absorbance of the dissolved compound was measured by BioTek Synergy HTX (Winooski, Vt., USA) microplate reader at 570 nm following standard procedure.

Statistics

All viability assays were repeated 3 times with at least 2 replicates each. Data was plotted by Microsoft Excel 2016 as the mean±standard error of the mean. A student t-test or a one-way analysis of variance (ANOVA) was used to check statistical significance where applicable. The differences were considered statistically significant for * $p<0.05$. A one-way multivariate analysis of variance (MANOVA) followed by a Post-Hoc test was used to check statistical significance where applicable.

Results and Discussion:

To systematically investigate the molecular basis for survival after CAP treatment by breast cancer cell lines which are classified into their intrinsic subtypes such as luminal A (ER+PR+/−HER2−), luminal B (ER+PR+/−HER2+), basal-like (ER−PR−HER2−), and HER2-positive (ER−PR−HER2+), we conducted quantitative real time PCR analysis to screen the genes that are differentially expressed after CAP treatment. We selected genes from four major categories based on their ability in "induction of apoptosis" (FIG. 7: Table 1), "regulation of apoptosis" (FIG. 8: Table 2), "caspases & regulators" (FIG. 9: Table 3) and "responders of oxidative stress" (FIG. 10: Table 4).

For the purpose of screening, we CAP treated triple negative breast cancer cell line MDA-MB-231 cells at 80 power and 120 power for 5mins and incubated at 37 C until isolating RNA at 3-, 6-, 12-, and 24-hour time points. Q RT-PCR were carried out for genes involved in the induction of apoptosis (FIG. 11), regulation of apoptosis (FIG. 12), caspase activation (FIG. 13) and regulation of oxidative stress (FIG. 14).

Figure 11:
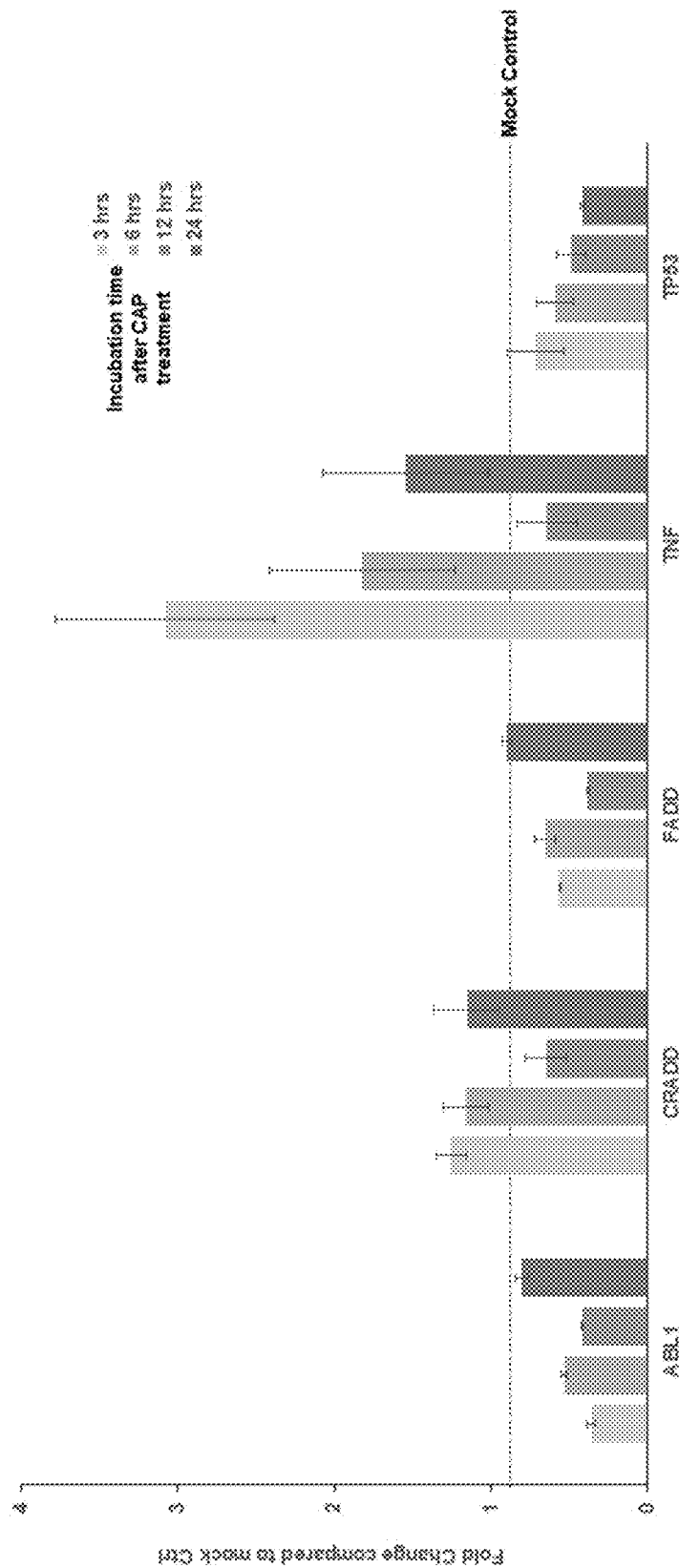
FIG. 11 is a bar graph showing the differential gene expression of genes involved in the induction of apoptosis after CAP treatment in triple negative breast cancer cell line MDA-MB-231.

FIG. 11 is a bar graph showing the differential gene expression of genes involved in the induction of apoptosis after CAP treatment in triple negative breast cancer cell line MDA-MB-231. The samples were normalized to 18s rRNA and the fold change were compared to mock controls (Represented by dotted line). Mann-Whitney test significant at p values <0.05.

ABL proto-oncogene 1, non-receptor tyrosine kinase (ABL1) aid in cell survival or trigger controlled cell death (apoptosis), depending on cellular conditions in response to DNA damage. Involved in intrinsic apoptotic signaling pathway via DNA damage. ABL1 mRNA expression is down regulated throughout the 24 hrs time point suggesting that apoptosis is initiated by 3 hrs time point by down regulating ABL1 in the CAP treated breast cancer cells. CASP2 and RIPK1 domain containing adaptor with death domain (CRADD)associates with PIDD1 and the caspase CASP2 to form the PIDDosome, a complex that activates CASP2 and triggers apoptosis. Also recruits CASP2 to the TNFR-1 signaling complex through its interaction with RIPK1 and TRADD and may play a role in the tumor necrosis factor-mediated signaling pathway2. CRADD is Involved in extrinsic apoptotic signaling pathway via death domain receptors. CRADD mRNA expression relatively unchanged at 3 hrs and 6 hrs time point and is down regulated at 12 hrs and returning to baseline condition suggest that CRADD is not involved in the induction of apoptosis in CAP treated breast cancer cells. FAS associated via death domain (FADD)a death domain-containing protein, interacts with the death domain of FAS and initiates apoptosis. FAS signaling complex through CASP8 activates cysteine protease cascade, leading to cell death. Involved in extrinsic apoptotic signaling pathway via death domain receptors. FADD mRNA expression is down regulated at 3 hrs, 6 hrs and 12 hrs time point and returning close to baseline condition at 24 hrs time point suggest that FADD is not involved in the induction of apoptosis in CAP treated breast cancer cells. Tumor Necrosis Factor (TNF)is a cell signaling protein (cytokine) involved in apoptotic cell death. Involved in extrinsic apoptotic signaling pathway via death domain receptors. TNF mRNA expression is relatively unchanged at 3 hrs and 6 hrs and up regulated at 12 hrs remains up regulated at 24 hrs suggest that TNF could be involved in the induction of apoptosis in CAP treated breast cancer cells. Tumor Protein p53 (TP53) is a nuclear transcription factor that regulates the expression of a wide variety of genes involved in apoptosis, growth arrest, or senescence in response to genotoxic or cellular stress. TP53 mRNA expression is down regulated throughout the 24 hrs incubation time suggesting that TP53 is not involved in the apoptosis of CAP treated breast cancer cells. mRNA expression of death associated protein kinase 1(DAPK1) a critical regulator of autophagy and apoptosis were not detected in CAP treated or control breast cancer cells.

Figure 12A:
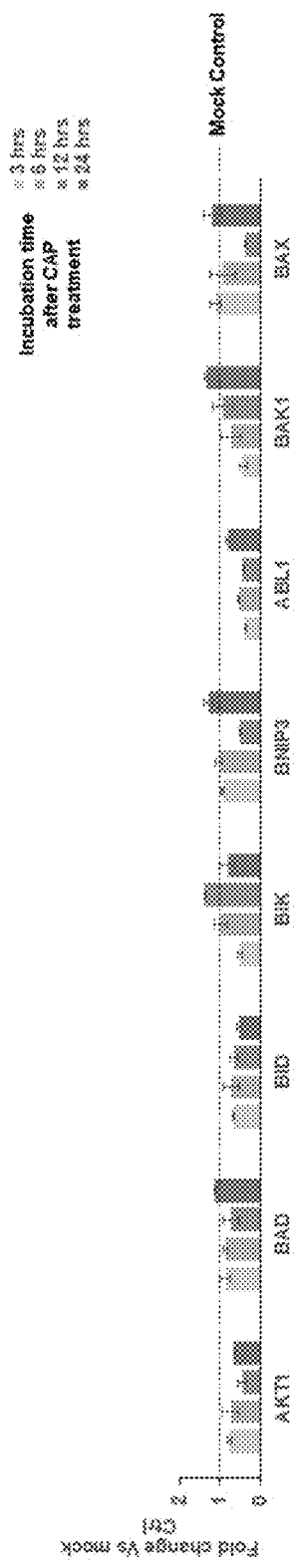
FIGS. 12A-12B are bar graphs showing the differential gene expression of genes involved in the positive (FIG. 12A) and negative (FIG. 12B) regulation of apoptosis after CAP treatment in triple negative breast cancer cell line MDAMB-231.
Figure 12B:
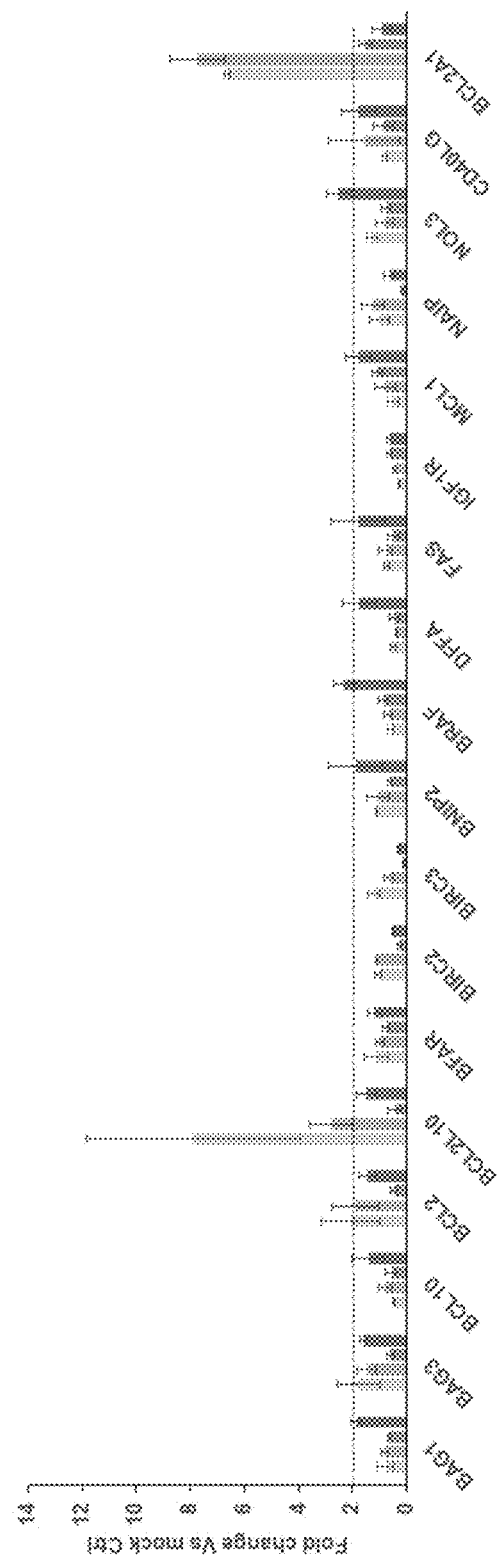

FIGS. 12A-12B are bar graph showing the differential gene expression of genes involved in the positive (FIG. 12A) and negative (FIG. 12B) regulation of apoptosis after CAP treatment in triple negative breast cancer cell line MDA-MB-231. The samples were normalized to 18s rRNA and the fold change were compared to mock controls (Represented by dotted line). Mann-Whitney test significant at p values <0.05. Vm41 AKT serine/threonine kinase 1 (AKT1) is an essential serine/threonine-specific protein kinase at the center of multiple cellular processes essential for cellular growth, metabolism, and survival. AKT1 mRNA expression is down regulated throughout the 24 hrs time point after CAP treated breast cancer cells. BCL2 associated agonist of cell death (BAD) induces apoptosis by inhibiting antiapoptotic BCL-2-family members—BCL-x, Bcl-2, thereby allowing two other pro-apoptotic proteins, BAK and BAX, to aggregate and induce release of cytochrome c, followed by caspase activation and apoptosis. BAD mRNA expression is relatively unchanged throughout the 24 hrs time point suggesting that the apoptosis CAP treatment on breast cancer cells does not involve BAD gene. BH3 interacting domain death agonist (BID) is a pro-apoptotic member of the Bcl-2 superfamily and as such possess the ability to target intracellular membranes and contains the BH3 death domain. BID mRNA expression is down regulated throughout the 24 hrs time point. BCL-2 Interaction Killer (BIK) gene is a pro-apoptotic member in the Bcl-2 gene family. Bik forms heterodimers with various anti-apoptotic proteins, including Bcl-2 and Bcl-XL, the association of which hinders the function of the anti-apoptotic proteins. BIK mRNA expression is down regulated at 3 hrs time point but steadily recovered above the baseline expression by the time point of 12 hrs and 24 hours incubation. BCL2 interacting protein 3 (BNIP3) is a member of the apoptotic Bcl-2 protein family that is involved an atypical, programmed cell death pathway resembling both necrosis and apoptosis. BNIP3 mRNA expression is relatively unchanged at 3 hrs and 6 hrs incubation after CAP treatment but is down regulated at 12 hrs and recovered above the baseline expression at the 24 hrs time point suggest that BNIP3 is involved in the late stages of apoptosis induced by the CAP treatment on breast cancer cells. BCL2 associated X, apoptosis regulator (BAX) is regulated by the tumor suppressor P53 and has been shown to be involved in P53-mediated apoptosis. BAX mRNA expression is remains at baseline levels at 3, 6 and 24 hrs incubation time point but is significantly down regulated at 12 hrs suggesting that BAX is differentially regulated during the last stage of the apoptosis process initiated by the CAP treatment on breast cancer cells. B-cell lymphoma 2 (BCL2) is a regulator protein that regulates cell death (apoptosis), by inhibiting (anti-apoptotic) apoptosis. BCL2 associated athanogene 3 (BAG3) is a membrane protein that blocks a step in a pathway leading to apoptosis or programmed cell death. Both BCL2 and BAG3 mRNA were up regulated at 3 and 6 hrs incubation time point and down regulated by 12 hrs time point and again up regulated at 24 hrs incubation time but this differentially regulation in response to the CAP treatment was not statistically significant. BCL2 associated athanogene 1 (BAG1) is a membrane protein that blocks a step in a pathway leading to apoptosis or programmed cell death. BCL2 like 10 (BCL2 L10) gene has been shown to suppress cell apoptosis possibly through the prevention of cytochrome C release from the mitochondria, and thus preventing caspase-3 activation. Bifunctional apoptosis regulator (BFAR) a multidomain protein that was originally identified as an inhibitor of Bax-induced apoptosis. MCL1, BCL2 family apoptosis regulator (MCL1) an anti-apoptotic member of the B-cell lymphoma 2 (Bcl-2) family of apoptosis-regulating proteins, exemplifies a number of the mechanisms by which a protein's contribution to cell fate may be modified. Nucleolar protein 3 (NOL3) an anti-apoptotic protein that has been shown to down-regulate the enzyme activities of caspase 2, caspase 8 and tumor protein p53. BAG1, BCL2 L10, BFAR, MCL1 and NOL3 mRNA expressions follow a similar trend by remaining at baseline levels at 3 and 6 hrs incubation time point but is slightly down regulated at 12hrs and up regulated at 24 hrs incubation time point. Even though differentially regulated during the later stage of the apoptosis process initiated by the CAP treatment they are not statistically significant. B-cell lymphoma 2-related protein Al (BCL2A1)/Bcl-2-related gene expressed in fetal liver (Bfl-1), is another member of the BCL-2 family of anti-apoptotic proteins that is associated with resistance to chemotherapeutics and targeted agents and functions as a lineage-specific oncogene by blocking cell death. BCL2A1 mRNA is significantly (p<0.0001) up regulated after at 3 and 6 hours after the CAP treatment suggesting BCL2A1 play an important role in the survival of breast cancer cells.

Figure 13A:
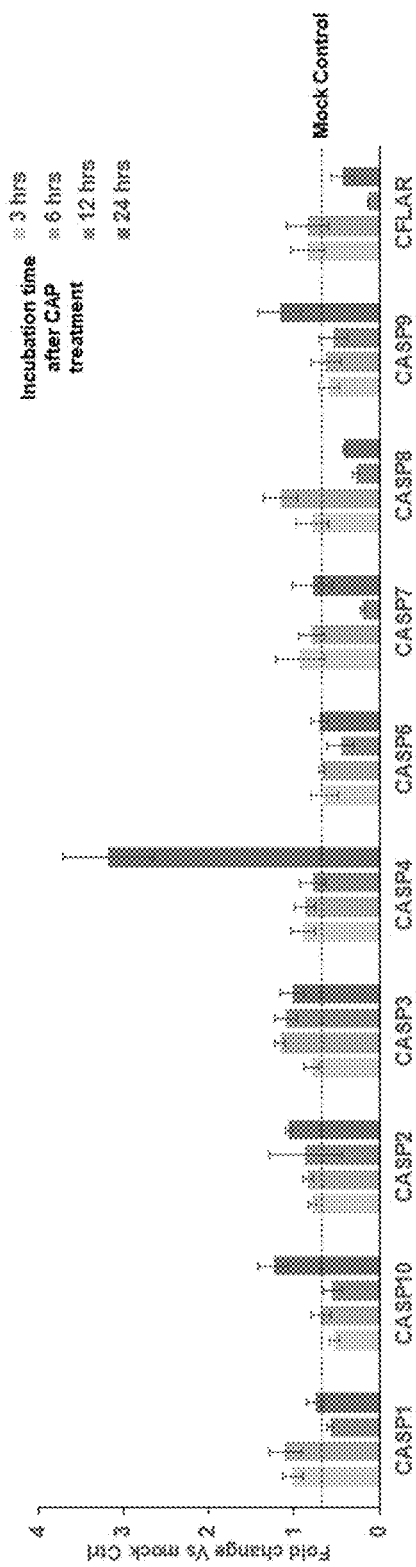
FIGS. 13A-13B are bar graphs showing the differential gene expression of genes involved in the caspase family (FIG. 13A) and caspase activation (FIG. 13B) regulation of apoptosis after CAP treatment in triple negative breast cancer cell line MDA-MB-231.
Figure 13B:
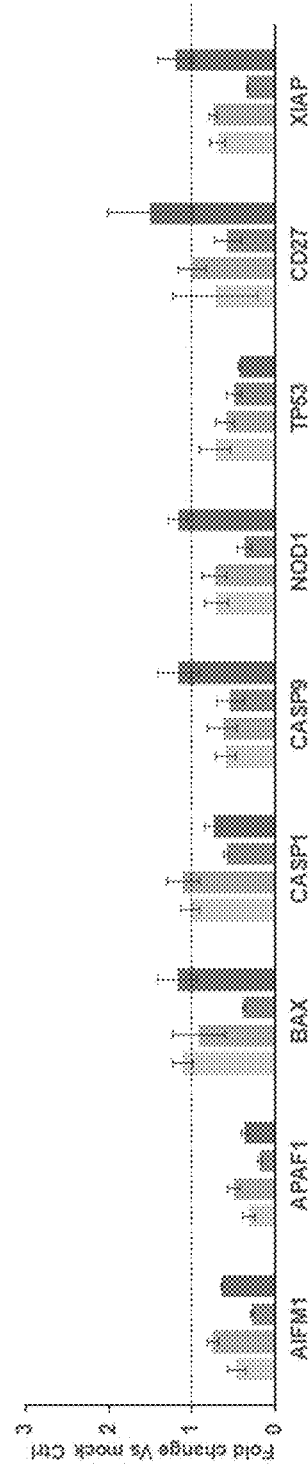
Figure 14:
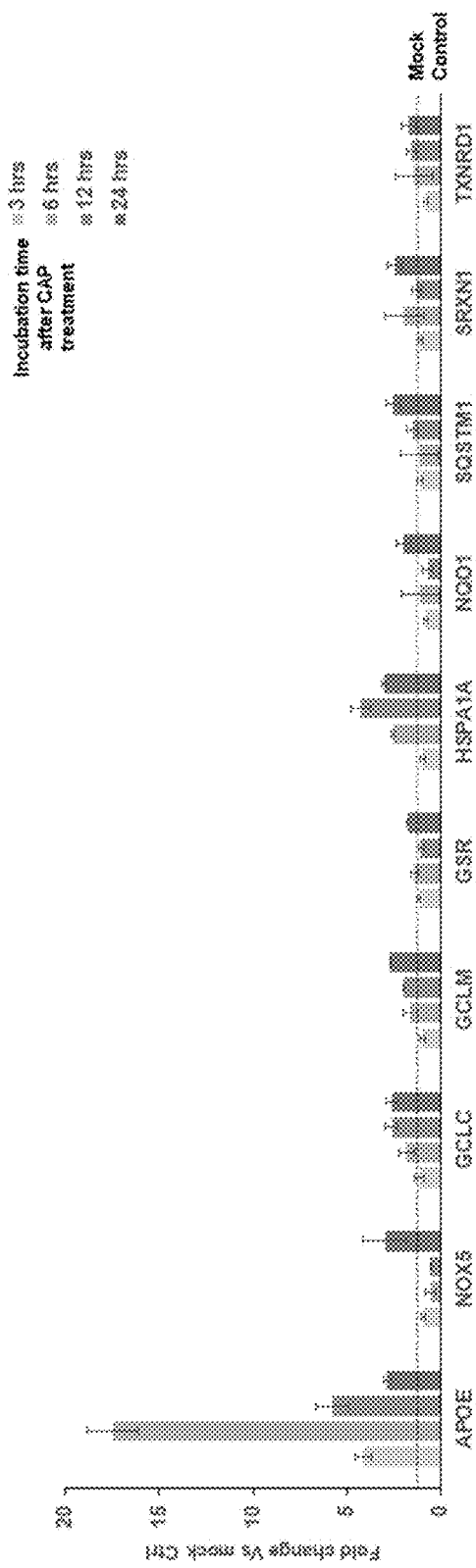
FIG. 14 is a bar graph showing the differential gene expression of genes involved in the regulation of oxidative stress after CAP treatment in triple negative breast cancer cell line MDA-MB-231.

FIGS. 13A-13B are bar graphs showing the differential gene expression of genes involved in the caspase family (FIG. 13A) and caspase activation (FIG. 13B) regulation of apoptosis after CAP treatment in triple negative breast cancer cell line MDA-MB-231. The samples were normalized to 18s rRNA and the fold change were compared to mock controls (Represented by dotted line). Mann-Whitney test significant at p values <0.05.

Caspase 1 (CASP1), Caspase-1/Interleukin-1 converting enzyme (ICE) can induce pyroptosis, a lytic form of cell death and also been shown to induce necrosis. Caspase 2, 4, 5, 7 and 8 are involved in the cascade of caspases responsible for apoptosis execution. Caspase 3 (CASP3) protein interacts with caspase-8 and caspase-9 and is activated in the apoptotic cell both by extrinsic (death ligand) and intrinsic (mitochondrial) pathways. Caspase 6 (CASP6) protein is processed by caspases 7, 8 and 10, and is thought to function as a downstream enzyme in the caspase activation cascade. Expect for CASP4 all the other Caspases that we analyzed were either unchanged or down regulated after CAP treatment.

FIG. 14: Bar graph showing the differential gene expression of genes involved in the regulation of oxidative stress after CAP treatment in triple negative breast cancer cell line MDA-MB-231. The samples were normalized to 18s rRNA and the fold change were compared to mock controls (Represented by dotted line). Mann-Whitney test significant at p values <0.05.

Among all the genes involved in oxidative stress (NOX5, GCLC, GCLM, GSR, NQO1, SQSTM1 and TXNRD1) Apolipoprotein E (APOE) was the only genes which up regulated significantly (p<0.001) after CAP treatment at 3-, 6-, 12-, and 24-hours incubation time point.

Figure 15A:
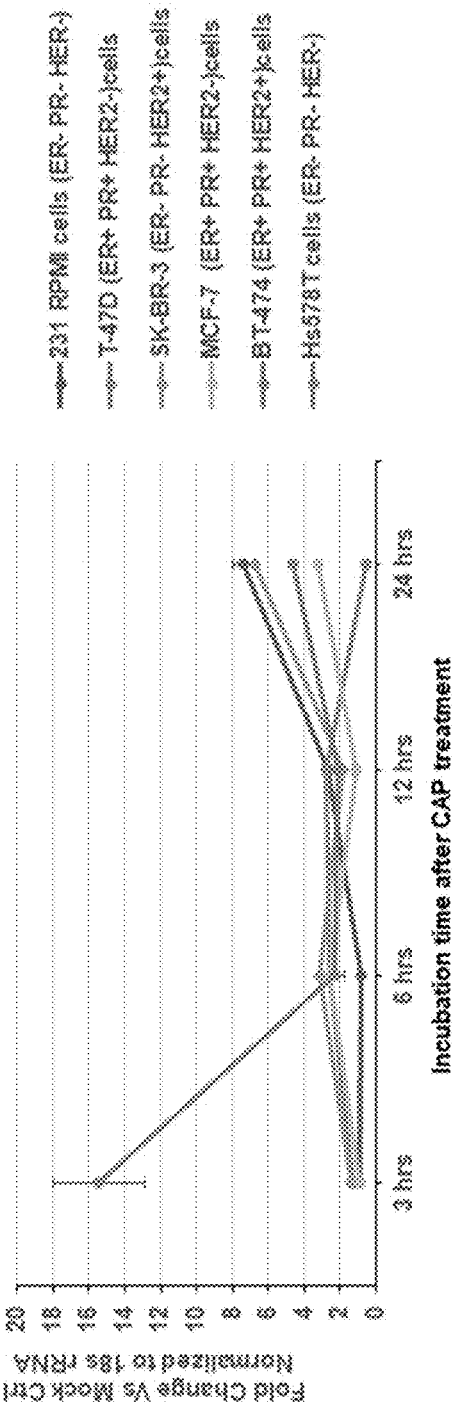
FIGS. 15A-15C are line graphs showing the differential gene expressions of BCL2A1 (FIG. 15A), TNF (FIG. 15B) and APOE (FIG. 15C) genes after CAP treatment at 120 power for 5 mins on breast cancer cell line MDA-MB-231.
Figure 15B:
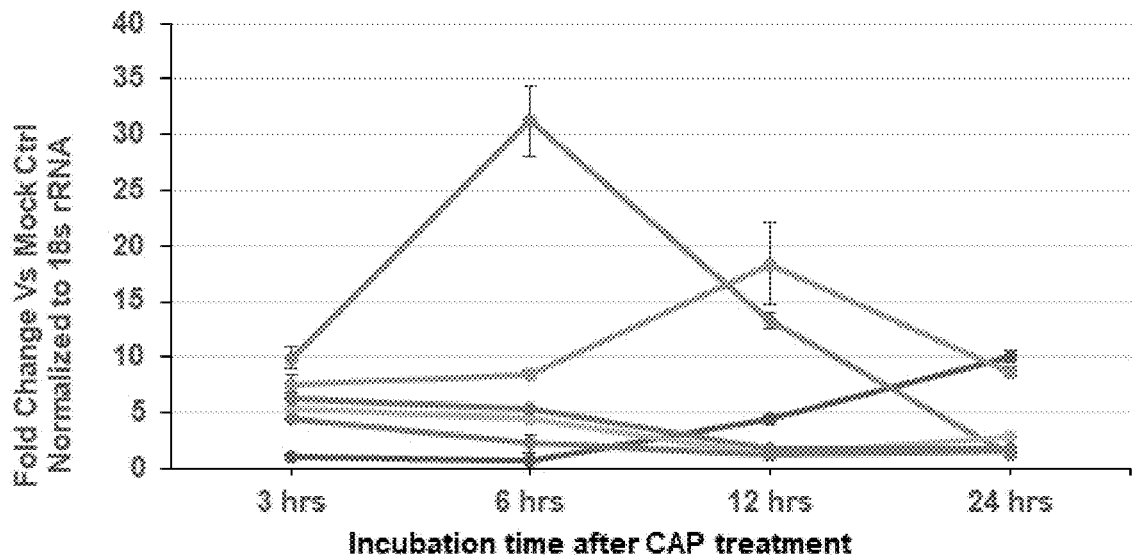
Figure 15C:
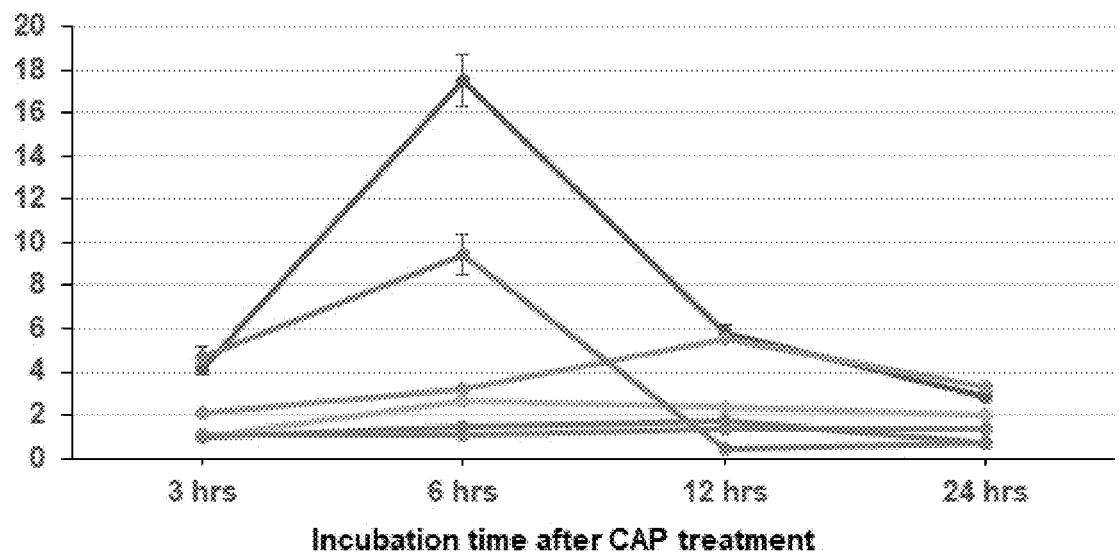

FIGS. 15A-15C are line graph showing the differential gene expression of BCL2A1 (FIG. 15A), TNF (FIG. 15B) and APOE (FIG. 15C) genes after CAP treatment at 120 power for 5 mins on breast cancer cell line MDA-MB-231. The samples were normalized to 18s rRNA and the fold change were compared to mock controls. Mann-Whitney test significant at p values <0.05.

Based on the initially gene profile screen after CAP treatment in triple negative breast cancer cells MDA-MB-231 cells three genes were further analyzed in other breast cancer cell lines MCF-7 (ER+, PR+, HER2−), T-47D 7 (ER+, PR+, HER2−), SK-BR-3(ER−, PR−, HER2+), BT-474 (ER+, PR+, HER2+), MDA-MB-231 (ER−, PR−, HER2−) and Hs574T (ER−, PR−, HER2−) (FIGS. 15A-15C). Triple negative cell line Hs574T showed significant up regulation of BCL2A1 in at 3 hrs after CAP treatment and remain above 2-fold increase up to 24 hours. T-47D 7, SK-BR-3 and BT-474 had very low detection levels of BCL2A1 expression. MCF-7 showed significant 2-fold up regulation of BCL2A1 at 6- and 24-hours' time points. TNF was significantly up regulated in all the cell lines at different time points for incubation after CAP treatment. The trend of BCL2A1 and TNF expressions were corelated in MDA-MB-231 and Hs574T cells suggesting a synergy in their regulation (FIGS. 16A-16B).

Figure 16A:
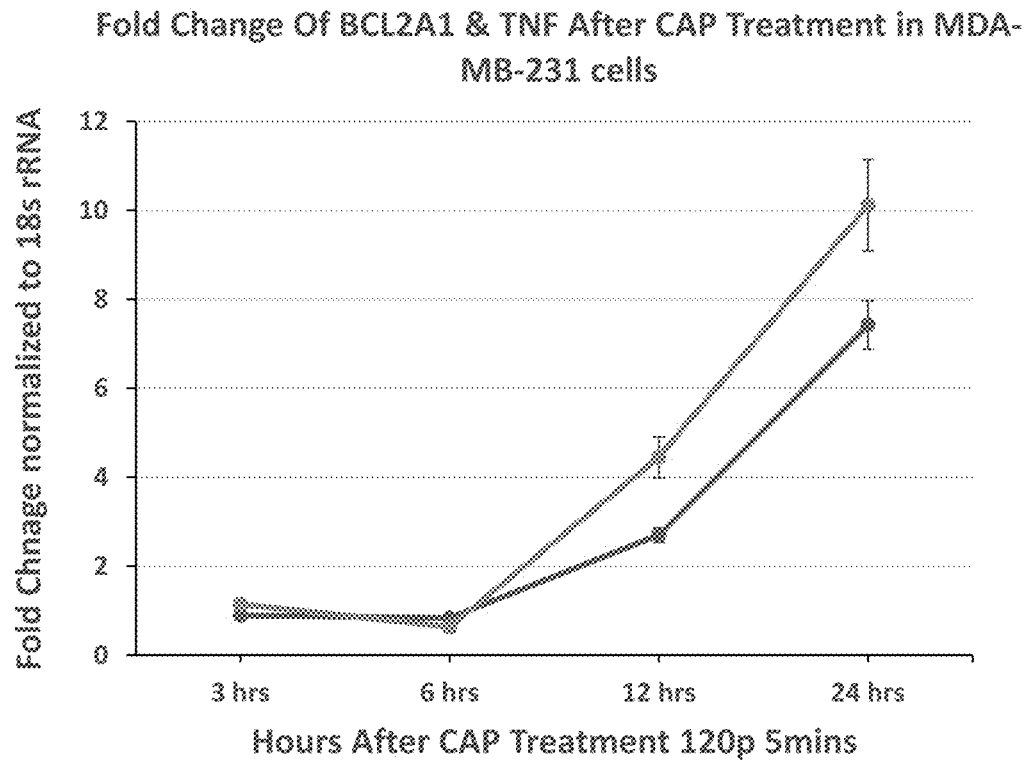
FIGS. 16A-16B are line graphs showing the correlation of BCL2A1 and TNF gene expression after CAP treatment at 120 power for 5 mins on two triple negative breast cancer cell line MDA-MB-231 (FIG. 16A) and Hs578T (FIG. 16B).
Figure 16B:
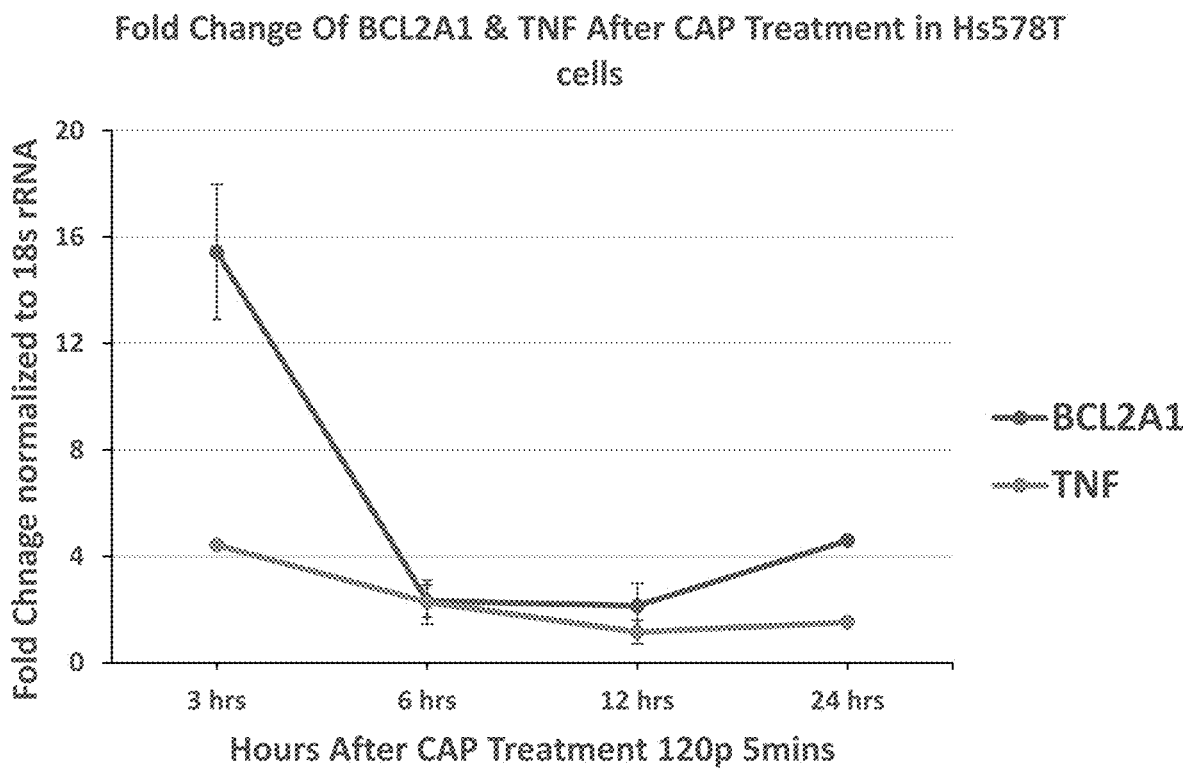

FIGS. 16A-16B are line graphs showing the correlation of BCL2A1 and TNF gene expression after CAP treatment at 120 power for 5 mins on two triple negative breast cancer cell line MDA-MB-231 (FIG. 16A) and Hs578T (FIG. 16B).

The samples were normalized to 18s rRNA and the fold change were compared to mock controls. Mann-Whitney test significant at p values <0.05.

Figure 17A:
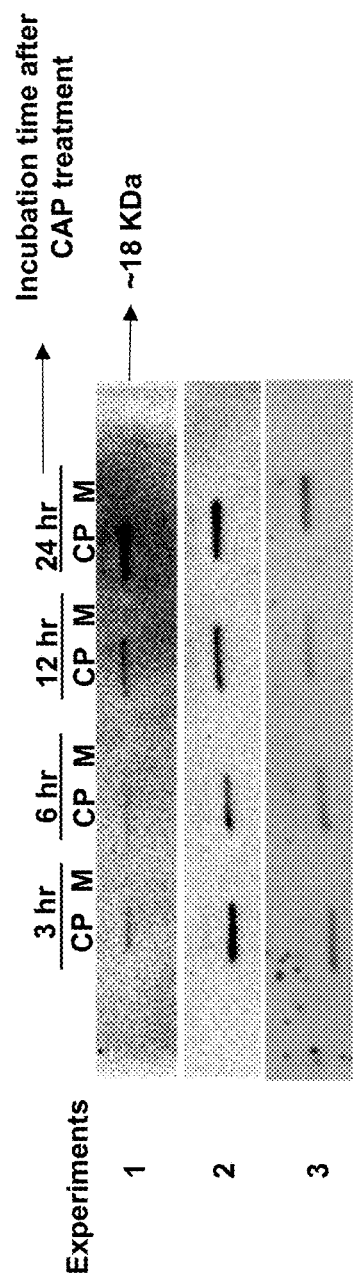
FIGS. 17A-17B are expressions of BCL2A1 after CAP treatment (CP) and mock controls (M) in triple cancer breast cancer cell line MDA-MB-231.
Figure 17B:
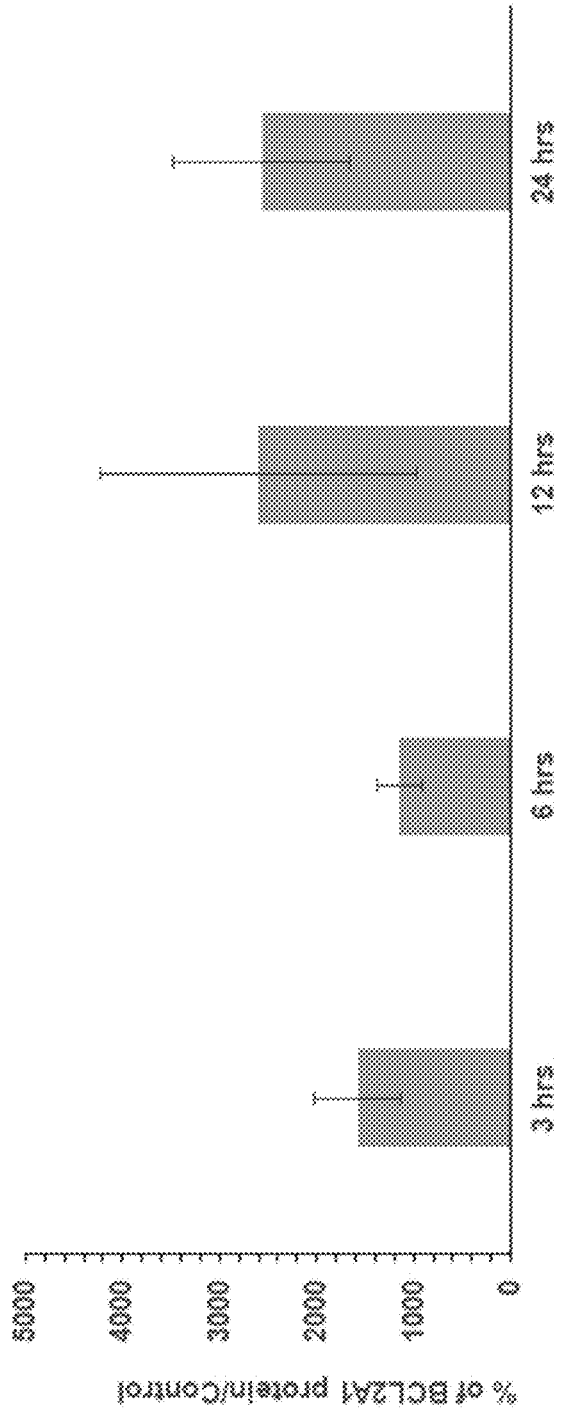

FIGS. 17A-17B show an expression of BCL2A1 after CAP treatment (CP) and mock controls (M) in triple cancer breast cancer cell line MDA-MB-231. Representative Western blots (FIG. 17A) and bar graph representation (FIG. 17B) of the quantification of BCL2A1 protein in total tissue lysates from MDA-MB-231 cells after CAP treatment compared to the mock control groups.

Western blot analysis also revealed an BCL2A1protein is expressed only after CAP treatment in triple negative breast cancer cells MDA-MB-231 cells and mock control cells did not show any protein bands (FIGS. 17A-17B). However, there were no significance in protein expression among 3-, 6-, 12- and 24-hours groups after CAP treatment.

Figure 18:
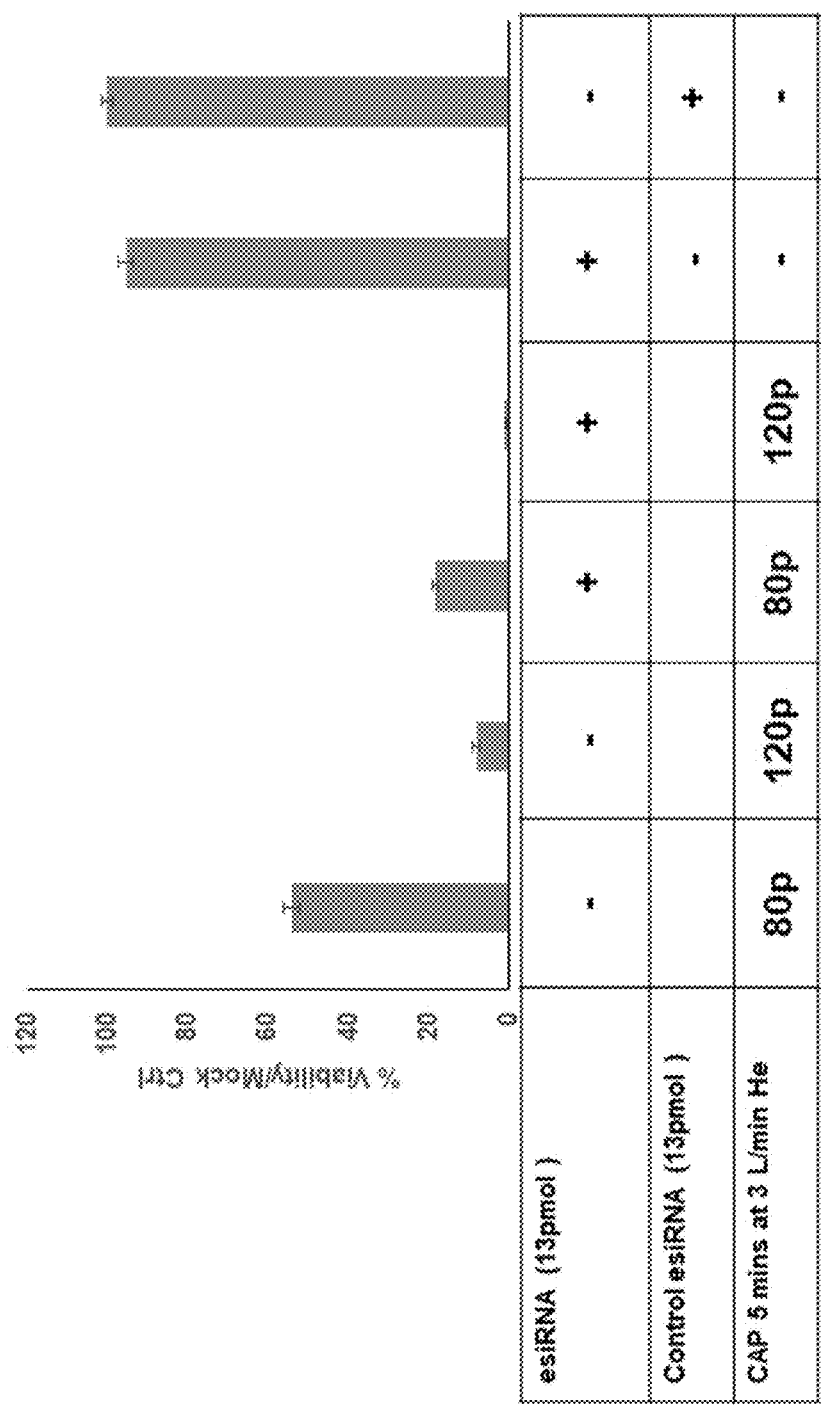
FIG. 18 is a bar graph illustrating effect of BCL2A1 esiRNA silencing in combination with CAP treatment on cell viability in MDA-MB-231 cell line.

FIG. 18 shows the effect of BCL2A1 esiRNA silencing in combination with CAP treatment on cell viability in MDA-MB-231 cell line. At 24 hrs after transfection with BCL2A1 esiRNA (13 pmol), as mentioned in methods section survival of treatments was determined by MTT assay. The data is represented by the SEM (n=3). (**** P<0.0001* p<0.05,  p<0.01, * p<0.001, Student's t-test) versus control.

Specific esiRNAs downregulate BCL2A1 mRNA expression in MDA-MB-231 cells. We examined the effect of silencing BC12A1 by esiRNA on the viability of MDA-MB-231 cells with and without CAP treatment. esiRNA has no effect on the MDA-MB-231 cells, but the in combination with esiRNA and CAP treatment the viability of cells significantly (p<0.001) reduced after 24 hours of treatment compared to either of the treatments alone (FIG. 18).

Figure 19A:
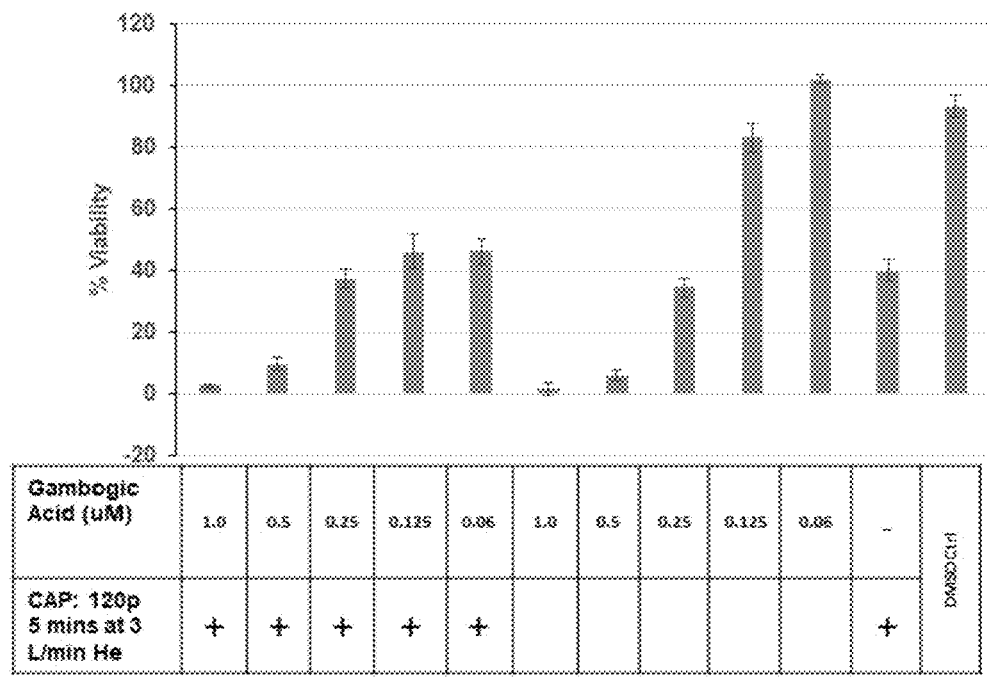
FIGS. 19A and 19B are bar graphs showing viability of triple cancer breast cancer cell line MDA-MB-231 with Gambogic acid, an antagonist of antiapoptotic Bcl-2 family (FIG. 19A) or CPI203 (FIG. 19B), a BET bromodomain inhibitor after CAP treatment.
Figure 19B:
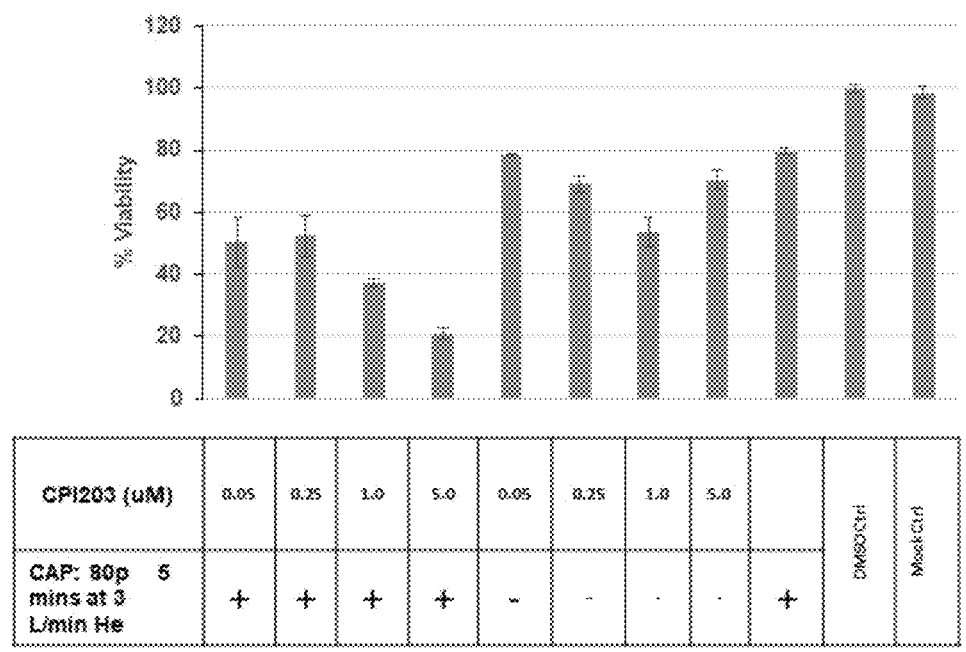

FIGS. 19A-19B show viability of triple cancer breast cancer cell line MDA-MB-231 with Gambogic acid, an antagonist of antiapoptotic Bcl-2 family (FIG. 19A) or CPI203 (FIG. 19B, a BET bromodomain inhibitor after CAP treatment. Bar graph represents MDA-MB-231 MTT cell viability assay after treatment with Gambogic acid (FIG. 19A) or CPI203 (FIG. 19B) in combination of with/without CAP treatment at 80 p Or 120 p 5 mins at 3 L/min He. The samples were compared to the mock control groups. The data is represented by the SEM (n=3). (* p<0.05,  p<0.01, * p<0.001, Student's t-test).

To determine the if gambogic acid (GA), an antagonist of antiapoptotic Bc1-2 family or CPI203, a BET bromodomain inhibitor that is previously shown to down regulate BCL2A1 would induce increased cell death after CAP treatment by inhibiting BCL2A1 protein. Baseline toxicity measurements were established for GA and CPI203. GA showed cell viability decreased in all the 5 doses test but there no dose that significantly reduced the viability of cells in combination with CAP treatment compared to CAP treatment alone. CPI203 showed significant reduction in cell viability at three dose concentrations (0.25 uM; * p<0.05), (1uM;  p<0.01) and (5uM; * p<0.001).

BCL2A1 expression plays an important role in the cell survival after CAP treatment in breast cancer cells. Silencing BCL2A1 by siRNA treatment or by down regulating it expression by CPI203 treatment in combination with CAP will significantly increase the potency of the CAP treatment. Based on our study a combination of CAP and anti-BCL2A1 immunotherapy would be beneficial for breast cancer therapeutic intervention.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for treating cancer comprising:
   treating a patient having a cancerous tumor with a gene inhibitor pre-operatively to inhibit upregulation of a particular gene;
   surgically removing the cancerous tumor;
   treating the patient with the gene inhibitor intra-operatively to inhibit upregulation of a particular gene;
   applying cold atmospheric plasma to surgical margins around the area in the patient from which the tumor was surgically removed; and
   treating the patient with the gene inhibitor post-operatively.

2. A method for treating cancer according to claim 1 wherein said cancer comprises triple negative breast cancer.

3. A method for treating cancer according to claim 1 wherein said particular gene comprises BCL2A1.

4. A method for treating cancer according to claim 1 wherein said pre-operative treating a patient with a gene inhibitor is within 24 hours of surgical removal of the cancerous tumor.

5. A method for treating cancer according to claim 1 wherein said post-operative treatment of a patient with a gene inhibitor is within 24 hours after surgical removal of the cancerous tumor.

6. A method for treating cancer according to claim 1 wherein said applying cold plasma comprises applying cold plasma at a power setting of 15 Watts.

* * * * *